(12) United States Patent
O'Phelan et al.

(10) Patent No.: US 6,763,265 B2
(45) Date of Patent: Jul. 13, 2004

(54) METHOD OF CONSTRUCTING A CAPACITOR STACK FOR A FLAT CAPACITOR

(75) Inventors: Michael J. O'Phelan, Oakdale, MN (US); James M. Poplett, Plymouth, MN (US); Robert R. Tong, Valencia, CA (US); A. Gordon Barr, Burnsville, MN (US); Richard J. Kavanagh, Brooklyn Park, MN (US); Brian V. Waytashek, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 10/418,616

(22) Filed: Apr. 17, 2003

(65) Prior Publication Data

US 2003/0195568 A1 Oct. 16, 2003

Related U.S. Application Data

(63) Continuation of application No. 09/705,994, filed on Nov. 3, 2000, now Pat. No. 6,571,126.

(51) Int. Cl.[7] ........................... A61N 1/02; H01G 9/022
(52) U.S. Cl. ................................ 607/5; 216/6; 216/33; 29/25.03
(58) Field of Search ........................... 607/5, 9, 17, 36; 361/502, 503, 517, 520, 523, 535; 29/25.01, 25.02, 25.03; 429/30, 94; 216/6, 33

(56) References Cited

U.S. PATENT DOCUMENTS

| | | | |
|---|---|---|---|
| 3,643,168 A | 2/1972 | Manicki | 455/178.1 |
| 3,723,926 A | 3/1973 | Thomas et al. | 335/268 |
| 3,777,570 A | 12/1973 | Thomas et al. | 73/701 |
| 3,826,143 A | 7/1974 | Thomas et al. | 73/701 |
| 3,828,227 A | 8/1974 | Millard et al. | 361/540 |
| 3,859,574 A | 1/1975 | Brazier | 361/520 |
| 3,938,228 A | 2/1976 | Kemkers et al. | 29/25.42 |
| 3,993,508 A | 11/1976 | Erlichman | 29/623.2 |
| 4,047,790 A | 9/1977 | Carino | 339/220 |
| 4,086,148 A | 4/1978 | Badia | 204/33 |
| 4,088,108 A | 5/1978 | Hager | 123/605 |
| 4,131,935 A | 12/1978 | Clement | 361/433 |
| 4,169,003 A | 9/1979 | Dangel et al. | 156/179 |
| 4,232,099 A | 11/1980 | Sullivan | 429/152 |
| 4,425,412 A | 1/1984 | Dittmann et al. | 429/53 |
| 4,553,304 A | 11/1985 | Fleuret | 29/25.42 |
| 4,571,662 A | 2/1986 | Conquest et al. | 361/306.1 |
| 4,659,636 A | 4/1987 | Suzuki et al. | 429/54 |
| 4,683,516 A | 7/1987 | Miller | 361/328 |
| 4,745,039 A | 5/1988 | Yoshinaka | 429/54 |
| 4,782,340 A | 11/1988 | Czubatyj et al. | 340/825.83 |

(List continued on next page.)

FOREIGN PATENT DOCUMENTS

| | | | |
|---|---|---|---|
| WO | WO-98/27562 | 6/1998 | |
| WO | WO-99/51302 | 10/1999 | A61N/1/375 |
| WO | WO-00/19470 | 4/2000 | |

*Primary Examiner*—Willis R. Wolfe
(74) *Attorney, Agent, or Firm*—Schwegman, Lundberg, Woessner & Kluth, P.A.

(57) ABSTRACT

In one aspect, a method of manufacturing a capacitor includes disposing one or more conductive layers of a first electrode stack in a recess of an alignment mechanism, where the recess is positioned relative to two or more alignment elements. The method further includes placing a separator over the one or more conductive layers where an outer edge of the separator contacts the two or more alignment elements. In one embodiment, a capacitor includes anode and cathode foils having offsetting edge portions. In one embodiment, a multiple tab cathode for a flat capacitor. A plurality of cathode tabs are portioned into a plurality of cathode tab groups positioned in different locations along the edge of the capacitor stack to reduce the amount of space required for connecting and routing the cathode tabs.

14 Claims, 23 Drawing Sheets

U.S. PATENT DOCUMENTS

| | | | |
|---|---|---|---|
| 5,131,388 A | 7/1992 | Pless et al. | 128/419 D |
| 5,173,375 A | 12/1992 | Cretzmeyer et al. | 429/72 |
| 5,175,067 A | 12/1992 | Taylor et al. | 429/181 |
| 5,306,581 A | 4/1994 | Taylor et al. | 429/181 |
| 5,422,200 A | 6/1995 | Hope et al. | 429/157 |
| 5,439,760 A | 8/1995 | Howard et al. | 429/94 |
| 5,471,087 A | 11/1995 | Buerger, Jr. | 257/532 |
| 5,507,966 A | 4/1996 | Liu | 252/62.2 |
| 5,522,851 A | 6/1996 | Fayram | 607/5 |
| 5,527,346 A | 6/1996 | Kroll | 607/5 |
| 5,584,890 A | 12/1996 | MacFarlane et al. | 29/25.03 |
| 5,628,801 A | 5/1997 | MacFarlane et al. | 29/25.03 |
| 5,640,756 A | 6/1997 | Brown et al. | 29/701 |
| 5,658,319 A | 8/1997 | Kroll | 607/7 |
| 5,660,737 A | 8/1997 | Elias et al. | 216/33 |
| 5,691,079 A | 11/1997 | Daugaard | 429/152 |
| 5,716,729 A | 2/1998 | Sunderland et al. | 429/66 |
| 5,754,394 A | 5/1998 | Evans et al. | 361/516 |
| 5,774,261 A | 6/1998 | Omori et al. | 359/464 |
| 5,776,632 A | 7/1998 | Honegger | 429/185 |
| 5,779,891 A | 7/1998 | Andelman | 210/198.2 |
| 5,800,724 A | 9/1998 | Habeger et al. | 216/35 |
| 5,801,917 A | 9/1998 | Elias | 361/535 |
| 5,811,206 A | 9/1998 | Sunderland et al. | 429/181 |
| 5,814,082 A | 9/1998 | Fayram et al. | 607/5 |
| 5,867,363 A | 2/1999 | Tsai et al. | 361/502 |
| 5,882,362 A | 3/1999 | Muffoletto et al. | 29/623.1 |
| 5,908,151 A | 6/1999 | Elias | 228/110.1 |
| 5,922,215 A | 7/1999 | Pless et al. | 216/6 |
| 5,926,357 A | 7/1999 | Elias et al. | 361/302 |
| 5,930,109 A | 7/1999 | Fishler | 361/508 |
| 5,963,418 A | 10/1999 | Greenwood, Jr. et al. | 361/508 |
| 5,968,210 A | 10/1999 | Strange et al. | 29/25.03 |
| 5,983,472 A | 11/1999 | Fayram et al. | 29/25.42 |
| 6,004,692 A | 12/1999 | Muffoletto et al. | 429/163 |
| 6,006,133 A | 12/1999 | Lessar et al. | 607/5 |
| 6,009,348 A | 12/1999 | Rorvick et al. | 607/5 |
| 6,030,480 A | 2/2000 | Face, Jr. et al. | 156/160 |
| 6,032,075 A | 2/2000 | Pignato et al. | 607/5 |
| 6,040,082 A | 3/2000 | Haas et al. | 429/163 |
| 6,042,624 A | 3/2000 | Breyen et al. | 29/25.03 |
| 6,094,788 A | 8/2000 | Farahmandi et al. | 25/24.41 |
| 6,099,600 A | 8/2000 | Yan et al. | 29/25.03 |
| 6,110,233 A | 8/2000 | O'Phelan et al. | 29/25.03 |
| 6,110,321 A | 8/2000 | Day et al. | 156/286 |
| 6,118,651 A | 9/2000 | Mehrotra et al. | 361/509 |
| 6,118,652 A | 9/2000 | Casby et al. | 361/517 |
| 6,139,986 A | 10/2000 | Kurokawa et al. | 429/61 |
| 6,141,205 A | 10/2000 | Nutzman et al. | 361/509 |
| 6,157,531 A | 12/2000 | Breyen et al. | 361/519 |
| 6,162,264 A | 12/2000 | Miyazaki et al. | 29/623.5 |
| 6,184,160 B1 | 2/2001 | Yan et al. | 438/800 |
| 6,191,931 B1 | 2/2001 | Paspa et al. | 361/302 |
| 6,212,063 B1 | 4/2001 | Johnson et al. | 361/517 |
| 6,225,778 B1 | 5/2001 | Hayama et al. | 320/112 |
| 6,249,423 B1 | 6/2001 | O'Phelan et al. | 361/502 |
| 6,275,729 B1 | 8/2001 | O'Phelan et al. | 607/5 |
| 6,297,943 B1 | 10/2001 | Carson | 361/500 |
| 6,299,752 B1 | 10/2001 | Strange et al. | 205/152 |
| 6,321,114 B1 | 11/2001 | Nutzman et al. | 607/5 |
| 6,388,866 B1 | 5/2002 | Rorvick et al. | 361/503 |
| 6,402,793 B1 | 6/2002 | Miltich et al. | 29/25.03 |
| 6,413,283 B1 | 7/2002 | Day et al. | 29/25.3 |
| 6,442,015 B1 | 8/2002 | Niiori et al. | 361/502 |
| 6,477,037 B1 | 11/2002 | Nielsen et al. | 361/520 |
| 6,493,212 B1 | 12/2002 | Clarke et al. | 361/215 |
| 6,509,588 B1 | 1/2003 | O'Phelan et al. | 257/209 |
| 6,522,525 B1 | 2/2003 | O'Phelan et al. | 361/509 |
| 6,571,126 B1 * | 5/2003 | O'Phelan et al. | 607/5 |
| 2001/0020319 A1 | 9/2001 | Farahmandi et al. | 29/25.03 |
| 2003/0077509 A1 | 4/2003 | Probst et al. | 426/162 |

* cited by examiner

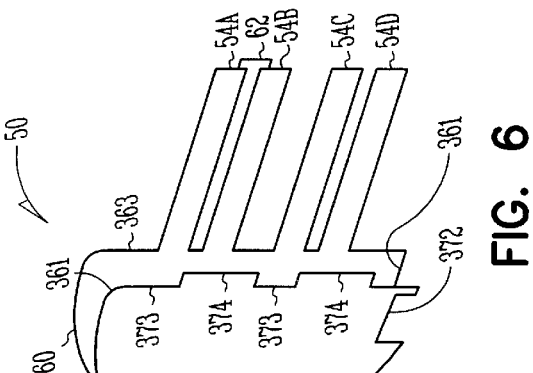
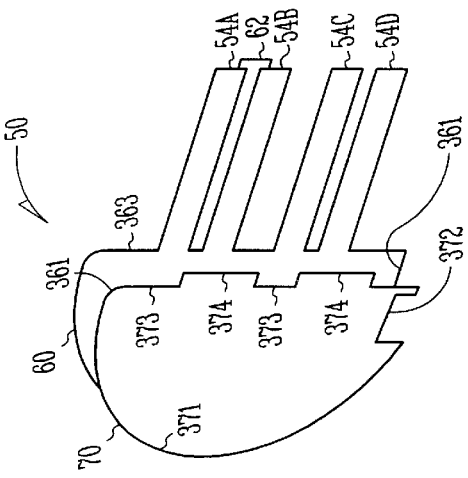
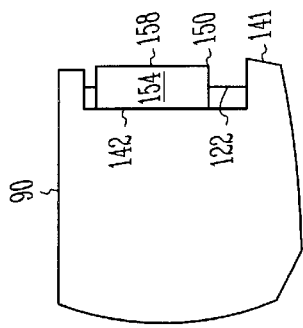
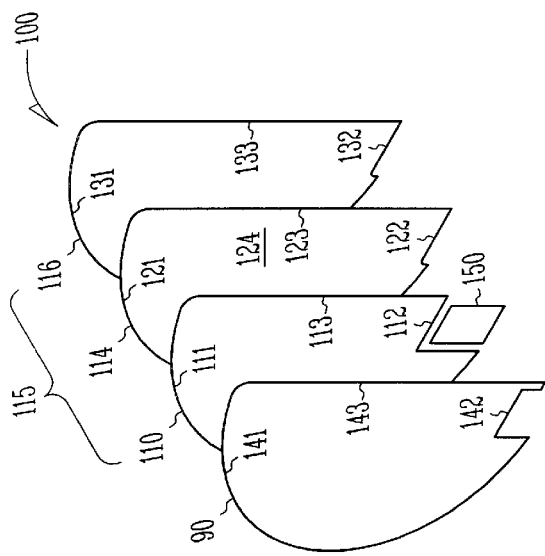

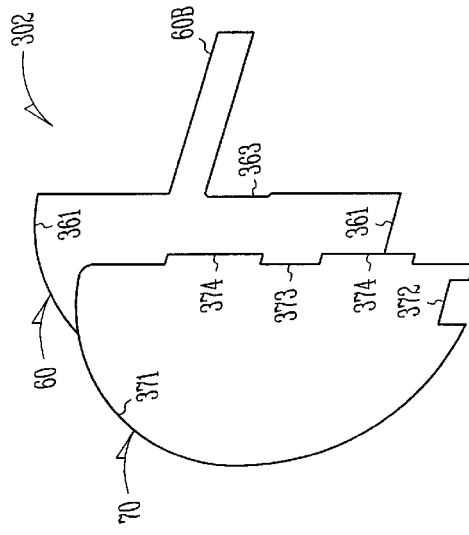
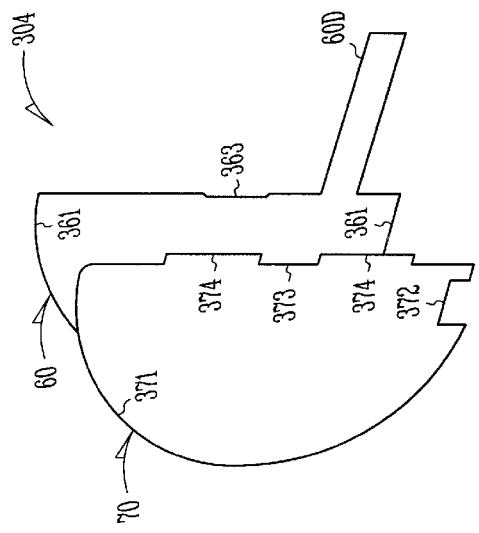
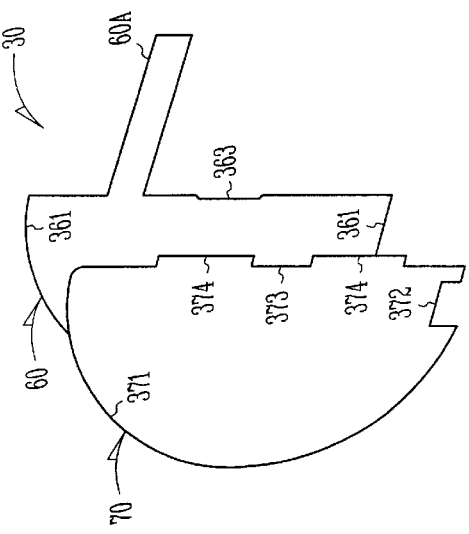
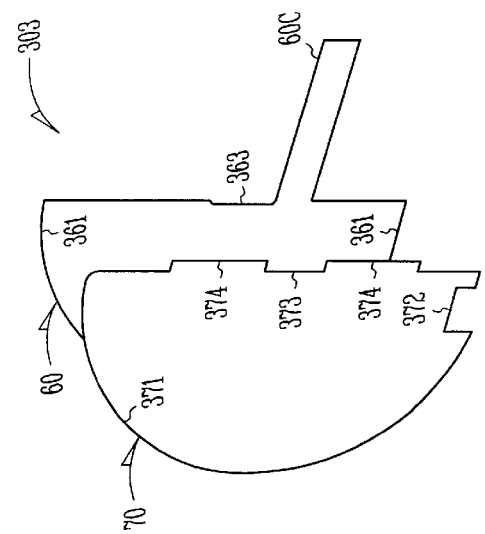

METHOD OF CONSTRUCTING A CAPACITOR STACK FOR A FLAT CAPACITOR

CROSS-REFERENCE TO RELATED APPLICATIONS

This application is a continuation of U.S. patent application Ser. No. 09/705,994, filed on Nov. 3, 2000, now U.S. Pat. No. 6,571,126, the specification of which is incorporated herein by reference.

This application is related to application Ser. No. 09/706,447, filed on Nov. 3, 2000, entitled FLAT CAPACITOR FOR AN IMPLANTABLE MEDICAL DEVICE, now U.S. Pat. No. 6,699,265, the specification of which is incorporated herein by reference in its entirety.

TECHNICAL FIELD

The present invention concerns implantable medical devices, such as defibrillators and cardioverters, and more specifically to a method of manufacturing a capacitor stack for a flat capacitor.

BACKGROUND

Since the early 1980s, thousands of patients prone to irregular and sometimes life-threatening heart rhythms have had miniature heart monitors, particularly defibrillators and cardioverters, implanted in their bodies. These devices detect onset of abnormal heart rhythms and automatically apply corrective electrical therapy, specifically one or more bursts of electric current to the heart. When the bursts of electric current are properly sized and timed, they restore normal heart function without human intervention, sparing patients considerable discomfort and often saving their lives.

The typical defibrillator or cardioverter includes a set of electrical leads, which extend from a sealed housing into the wall of a heart after implantation. Within the housing are a battery for supplying power, monitoring circuitry for detecting abnormal heart rhythms, and a capacitor for delivering bursts of electric current through the leads to the heart.

Flat capacitors generally include a stack of flat capacitor elements, with each element including a paper separator between two sheets of aluminum foil. One of the foils serves as the anode of the capacitor element, and the other serves as the cathode.

One or more of the capacitor elements are often die cut in a shape designed to conform to a capacitor case. The cutting results in undesired residual stresses, and in warpage of the capacitor element. Stacking a plurality of these types of capacitor elements may result in increased height to the assembly. Moreover, the foil strip used to produce the capacitor element may not have the desired flatness prior to processing. Undesired residual stress due to this factor may also result in warpage of the capacitor assembly, enough to add height to the assembly. Moreover, the foils are cut using high-precision dies which are not only expensive, but require repeated sharpening. Another problem that arises is that cutting the foils can produce burrs on the cut edges of the foils. When edge burrs on adjacent anode and cathode foils contact each other, a conductive path results that short circuits the capacitive element.

Each anode foil in the stack, and each cathode foil in the stack, is interconnected to the other anodes and cathodes respectively. The anodes and cathodes generally include tabs which are crimped or welded together. Connecting the anodes and cathodes in this way provides a total capacitance equal to the sum of the capacitances of all the capacitor elements. However, the anode and cathode interconnections cause designers to increase the size of the capacitor case to accommodate tabs or to remove a portion of the capacitive elements, which reduces total capacitance or increases the size of the capacitor.

Moreover, since defibrillators and cardioverters are typically implanted in the left region of the chest or in the abdomen, a smaller size device, which is still capable of delivering the required level of electrical energy, is desirable.

Accordingly, there is a need for capacitor structures and methods of manufacture which provide greater process control, less expensive manufacturing, provide for a design efficiently utilizing space within the capacitor case, and provide for a compact capacitor design capable of providing the required pulse of energy for use within the implantable device.

SUMMARY

In one embodiment, a method of manufacturing a capacitor includes disposing one or more conductive layers of a first electrode stack in a recess of an alignment mechanism, where the recess is positioned relative to two or more alignment elements. The method further includes placing a separator over the one or more conductive layers where an outer edge of the separator contacts the two or more alignment elements. In addition, the method includes securing the aligned separator and conductive layers to one another to form an anode or a cathode stack.

In one embodiment, a method of manufacturing a capacitor includes providing an alignment mechanism having a plurality of alignment elements and a recess, each alignment element having a position corresponding to a point on the outer edge of either a first electrode stack or second electrode stack. The method further comprises aligning a portion of at least one first electrode stack relative to the recess and the alignment elements, and removing the aligned first electrode stack. In addition, the method further includes aligning a portion of at least one second electrode stack relative to a second alignment mechanism including a second recess and second alignment elements. The method further includes removing the aligned second electrode stack.

One aspect provides a multi-tab base foil layer for a flat capacitor. The base tabs of the base foil layer are spaced laterally along a vertical face of the capacitor stack. In addition to the base layer, the capacitor stack of foil layers includes secondary layers. The secondary layers have matching tabs that overlay the base tabs of the base layer. In one embodiment, this arrangement reduces the space required for connecting and routing the tab groups and this allows a reduction in the size of the capacitor, or alternatively an increase in its capacitance, or energy-storage capacity.

One aspect provides a capacitor stack structure that is more tolerant of edge burrs in the cut foil layers. In one embodiment, a capacitor with anode and cathode layers having non-overlapping edge portions. The cathode and anode layers are shaped or positioned such that edge portions of the two layers are offset from one another in a layered structure.

In one or more embodiments, the above described methods and structures provide for a capacitor making efficient use of space within the case, increased anodic surface area and increased capacitance for a capacitor of a given set of dimensions. Variation in the outer dimensions of one capacitor stack to another capacitor stack is reduced because each is formed within alignment elements positioned the same manner. Dimensional variations in the capacitor stack resulting from variation in the reference points from case to case or alignment apparatus to alignment apparatus are eliminated. This provides improved dimensional consistency in production and allows for reduced tolerances between the capacitor stack and the capacitor case. This allows for more efficient use of space internal to the capacitor case.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

BRIEF DESCRIPTION OF DRAWINGS

FIG. 3 is an exploded perspective view of an anode stack constructed in accordance with one embodiment.

FIG. 4 is a side view of an anode stack and edge connection member constructed in accordance with one embodiment.

FIG. 5 is a side view of a separator constructed in accordance with one embodiment;

FIG. 6 is an exploded perspective view of a cathode base layer stack constructed in accordance with one embodiment.

FIG. 7 is an exploded perspective view of a cathode stack constructed in accordance with one embodiment.

FIG. 8 is an exploded perspective view of a cathode stack constructed in accordance with one embodiment.

FIG. 9 is an exploded perspective view of a cathode stack constructed in accordance with one embodiment.

FIG. 10 is an exploded perspective view of a cathode stack constructed in accordance with one embodiment.

DESCRIPTION OF EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
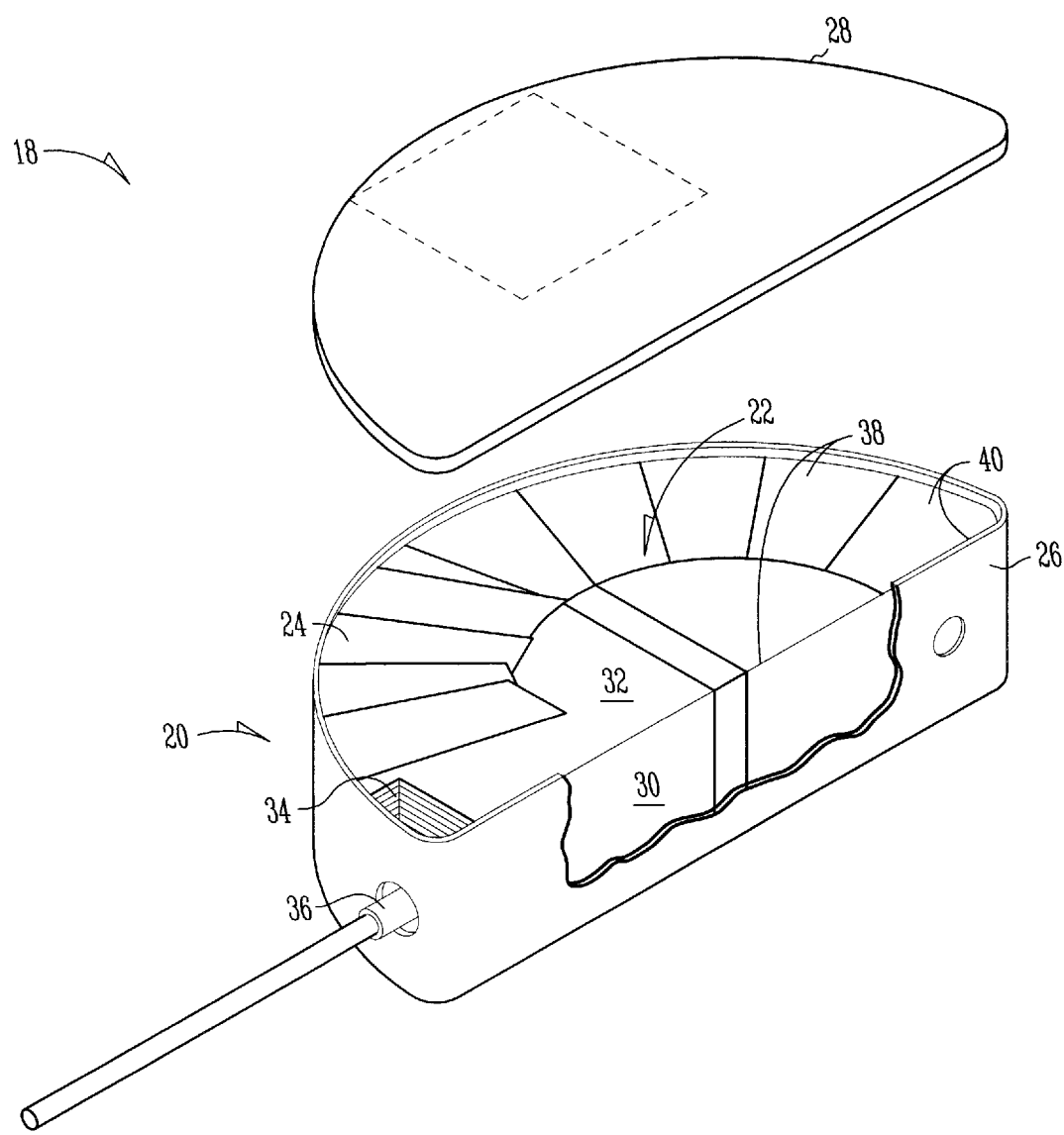
FIG. 1 is a perspective view of a flat capacitor according to one embodiment of the present invention.

FIG. 1 shows a partially exploded view of an exemplary embodiment of capacitor 18. The present embodiment shows a D-shaped capacitor. In other embodiments, capacitor 18 may be designed in a variety of flat shapes to conform to various housing shapes. The capacitor includes a metallic case 20 defining a chamber 22, in which is placed a capacitor stack 24. In one embodiment, case 20 is manufactured from a conductive material, such as aluminum. In another option, the case 20 is manufactured using a nonconductive material, such as a ceramic or a plastic.

Case 20 includes a base 26 and a lid 28 overlying and resting on an upper rim of base 26. Stack 24 has a face 30 and a top surface 32. Stack 24 has a cutout region 34 at its periphery, with cutout region 34 being positioned when the stack 24 is installed in case 20 to provide space for electrical connections. An anode feedthrough post 36 passes through to stack 24 and is electrically insulated from case 20. The capacitor stack 24 is covered with insulating tape 38. A space 40 exists between the lid 28 and the top surface 32 of the stack 24 and between the face 30 of the stack 24 and a lateral wall of the base 26 of the case 20. In some embodiments, space 40 is a line-to-line interference fit between portions of stack 24 and case 20. In other embodiments, space 40 is a gap or opening within the case and between the stack and the case.

Capacitor stack 24 includes anode assemblies and cathode assemblies, with separator layers interposed therebetween.

Figure 2:
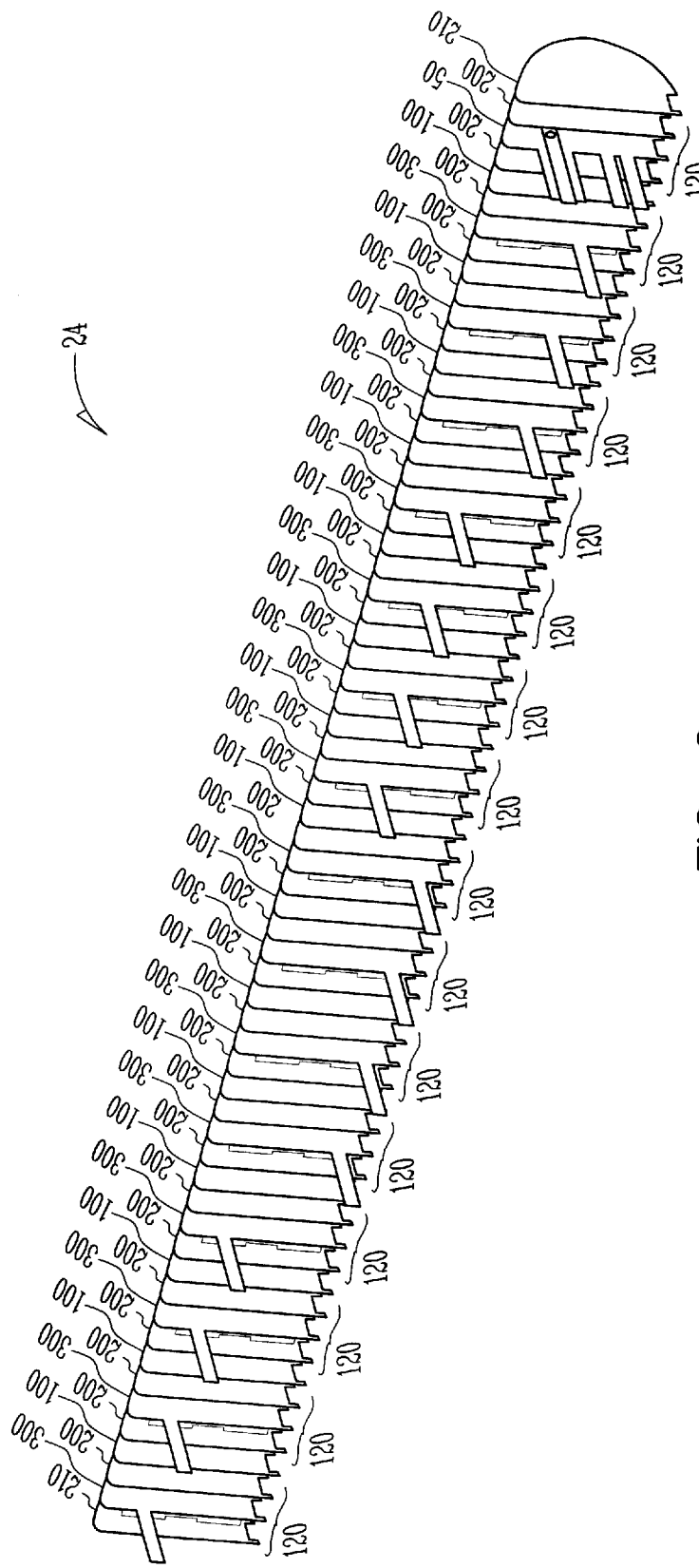
FIG. 2 is an exploded perspective view of a capacitor stack constructed in accordance with one embodiment.

FIG. 2 illustrates an exploded view of capacitor stack 24 according to one embodiment. Stack 24 includes a plurality of layers 120 which include at least one first electrode comprised of an anode stack 100, at least one separator 200, and at least one second electrode comprised of one of cathode stacks 300. The separator 200 separates each anode stack 100 from each cathode stack 300.

FIG. 3 illustrates an exploded view of one example of an anode stack 100. The anode stack 100 includes a plurality of anode layers including conductive layers 115 consisting of an upper conductive layer 110, a middle conductive layer 114, and a lower conductive layer 116 as well as an anode-separator layer 90. Each conductive anode layer has a first edge 111, 121, 131, and 141, respectively. Each anode layer also includes a clearance area defined by a second edge 112, 122, 132, 142. Each anode layer also includes an optional second edge 113, 123, 133, 143, respectively. The anode stack 100 further includes an edge connection member such as edge clip 150 for use in interconnecting the anode layers in adjacent layers of the capacitor stack 24.

FIG. 4 illustrates a portion of an assembled anode stack 100. The clearance area defined by the second edge 142 of the anode-separator 90 leaves the upper surface 154 of the edge clip 150 exposed for contact with an adjacent edge clip 150 of an adjacent layer 120.

FIG. 5 illustrates a separator 200 which separates the anode stack 100 from the cathode stack 300 (FIG. 2). The separator 200 includes a first edge 251 a clearance area defined by a second edge 252 and a flat edge 253. The clearance area of the separator 200 allows a side portion of the edge clip 150 (FIG. 3) to extend past the separator to reach an edge clip of an adjacent anode stack 100 (FIG. 2). The separator 200 is, in one option, made from a roll or sheet of separator material. Suitable materials for the separator material include, but are not limited to, pure cellulose or Kraft paper. Other chemically inert materials are suitable as well, such as porous polymeric materials. The separator 200 is cut slightly larger than the anode layers (or cathode layers) to accommodate misalignment during the stacking of layers, to prevent subsequent shorting between electrodes of opposite polarity, and to act as an outermost edge for alignment.

FIG. 6 illustrates an exploded view of an embodiment of a cathode base stack 50 including a cathode conductive layer 60 and a cathode-separator layer 70. In this embodiment, cathode conductive layer 60 includes one or more legs 54a, 54b, 54c, 54d extending from the flat edge 363. The cathode conductive layer 60 also includes a cathode extension member 62 for coupling the capacitor stack 24 to the case 20 (FIG. 1). Cathode legs 54a, 54b, 54c, 54d and cathode extension leg 62 extend beyond the dimensions defined by the inside of the case 20 during intermediate steps in the manufacturing process and are later formed to fit within the case. The cathode conductive layer 60 includes a first edge 361 inset from the first edges of the anode layers 110, 114, 116, and 90 (FIG. 3) and inset from the second edges of the anode layers 110, 114, 116, and 90. The conductive layer 60 also includes a flat edge 363 inset from the flat edges of the anode layers 110, 114, 116, and 90.

Cathode-separator layer 70 is also provided and includes a first edge 371, a clearance area defined by a second edge 372, a flat edge 373 and an extension edge 374. The cathode conductive layer 60 includes a first edge 361 inset from the first edge 371 of the cathode-separator and inset from the second edges of the cathode-separator layer 70. The cathode conductive layer 60 also includes a flat edge 363 inset from the flat edges of the cathode-separator layer 70. The inset edge 361 of the cathode conductive layer 60 and the clearance area of the cathode-separator layer 70 allows a portion of the edge clip 150 (FIG. 3) to extend past the cathode conductive layer 60 and the cathode-separator layer 70 to reach an edge clip 150 (FIG. 3) of an adjacent anode stack.

Referring to FIGS. 7–10, examples of cathode stacks 300 are shown. Cathode stacks 300 include in one embodiment, cathode stacks 301, 302, 303, 304. Each cathode stack 301, 302, 303, 304 includes cathode layers comprising a cathode conductive layer 60 and a cathode-separator layer 70. In this embodiment, each cathode stack 301, 302, 303, 304 conductive layer 60 includes an extension member such as a leg 60a, 60b, 60c, or 60d respectively. Cathode legs 60a–60d on each cathode stack 301, 302, 303, 304 extend beyond the dimensions defined by the case 20 (FIG. 1) during intermediate steps in the manufacturing process and are later formed to fit within the case. In one embodiment, each leg 60a–60d corresponds to leg 54a, 54b, 54c, 54d, respectively, on the cathode base layer stack 50, as will be discussed further below. Each cathode stack 301, 302, 303, 304 includes a cathode conductive layer 60 having a first edge 361, which when stacked, is inset from the first edge 141 of the anode separator 90 (FIG. 3) and inset from the second edge 142 of the anode separator. Further details of cathode stacks 300 will be described below.

In one embodiment of the present invention, the capacitor stack 24 described above is aligned to provide for optimal surface area of the capacitor.

Figure 11A:
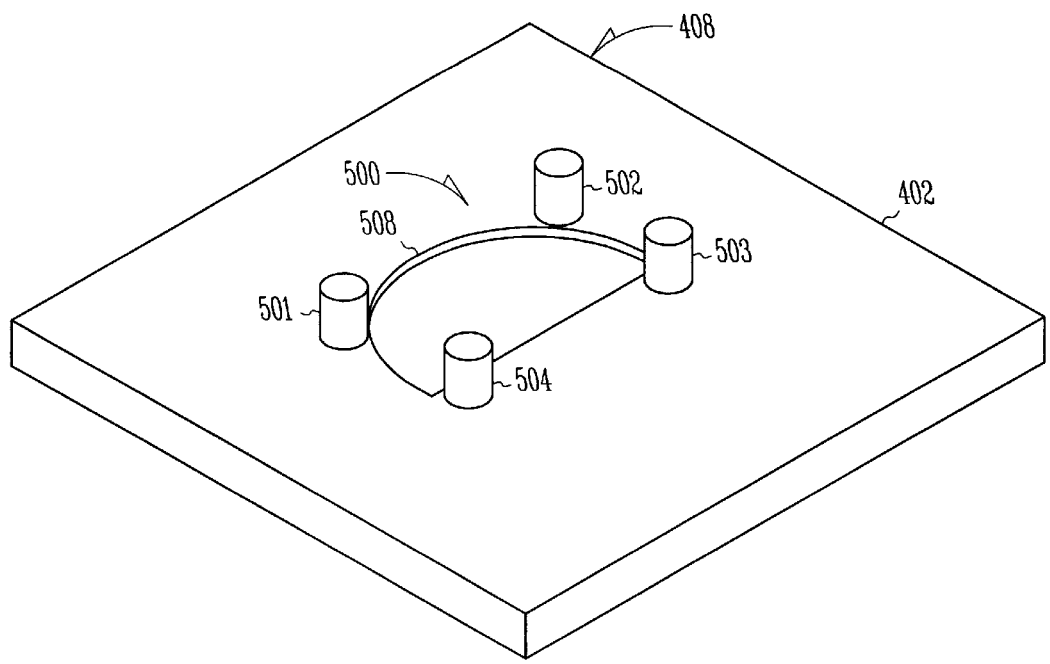
FIG. 11A is a perspective view of an alignment mechanism constructed in accordance with one embodiment.
Figure 11B:
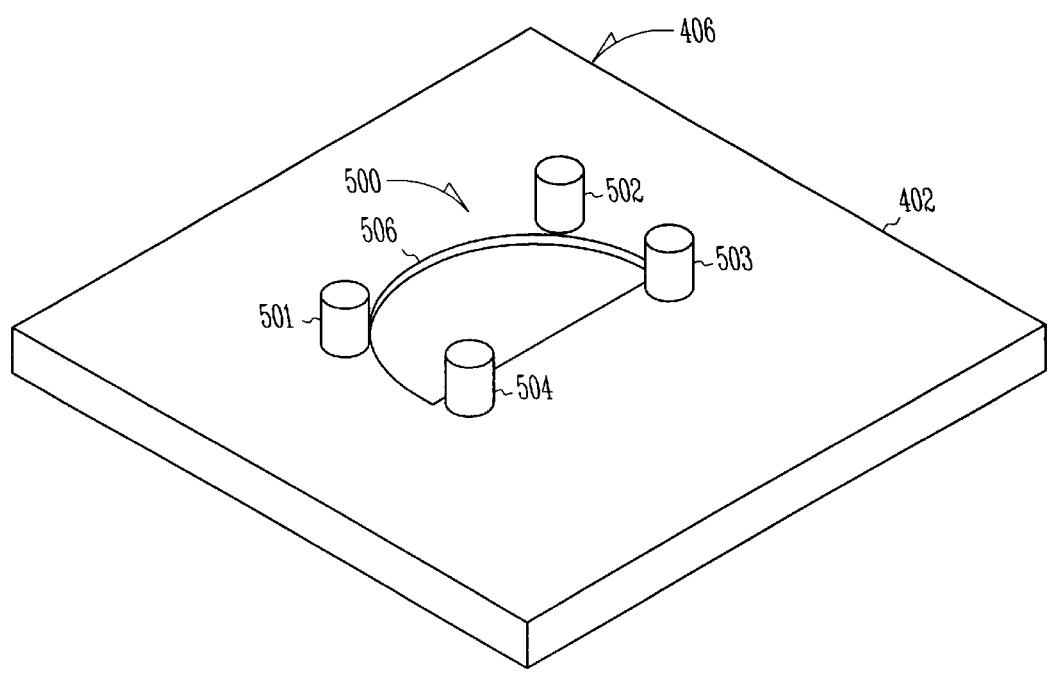
FIG. 11B is a perspective view of an alignment mechanism constructed in accordance with one embodiment.
Figure 12:
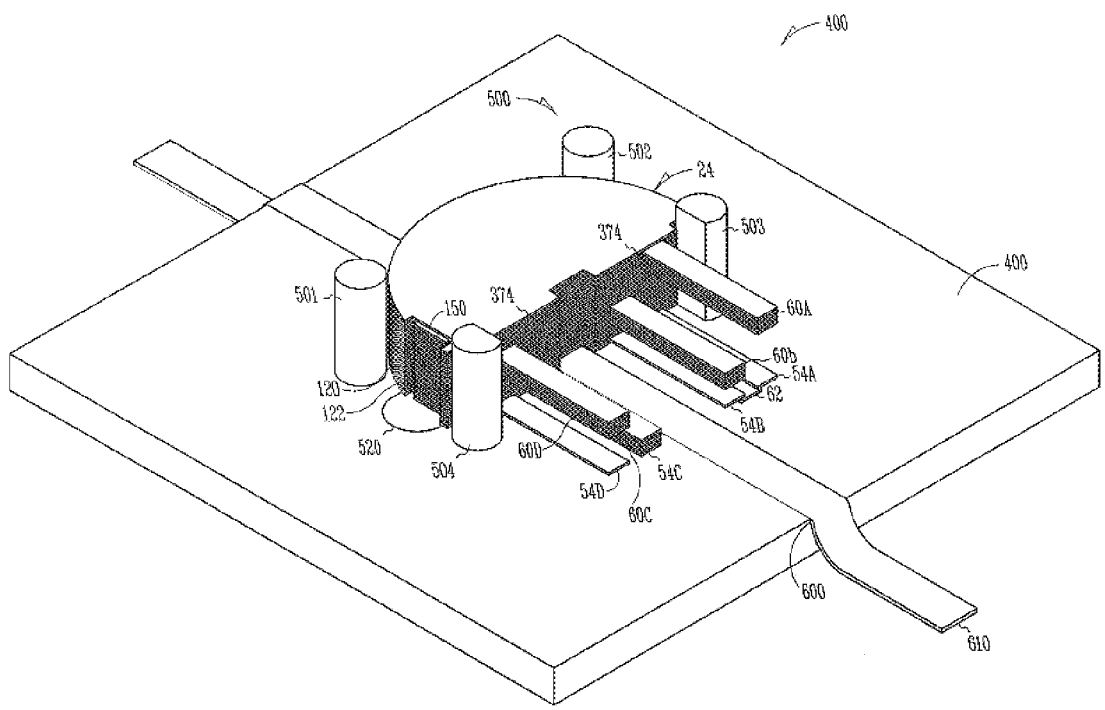
FIG. 12 is a perspective view of a capacitor stack in an alignment mechanism constructed in accordance with one embodiment.

FIGS. 11A, 11B, and 12 illustrate external alignment mechanisms 408, 406, 400 used to assemble anode stack 100, cathode stack 300, and capacitor stack 24, respectively, in accordance with one embodiment. Each of the external alignment mechanisms 408, 406, 400 includes a plurality of precisely placed alignment elements 500.

The alignment elements 500 in this embodiment, are vertically placed alignment elements 501, 502, 503, 504, which extend from a base 402. The base 402 supports components thereon, while the alignment elements 501, 502, 503, 504 align the components while the components are being stacked therein. The external alignment mechanism 400 optionally includes a first recess 520, which is sized and positioned to receive a clip, as further discussed below. In another option, the external alignment mechanisms 406, 408 each include a second recess 506, 508, respectively, in the base 402, as further discussed below.

Referring to FIG. 12, a capacitor stack 24 is assembled within the alignment apparatus 400. The capacitor stack 24 includes the plurality of layers 120. Each layer 122 of the plurality of layers 120 includes at least one first electrode stack, at least one separator 200 (FIG. 2) and at least one second electrode stack. Each first electrode stack, second electrode stack and each separator 200 is aligned relative to the position of the alignment elements 501, 502, 503, and 504. Optionally positioned within the optional channel 600 is a fastener 610, which is for wrapping around a portion of the capacitor stack 24 once the first electrode stacks, separators 200 and second electrode stacks have been stacked and aligned. Placing the fastener 610 in the channel 600 of the external alignment mechanism 400 positions the fastener 610 below the aligned capacitor stack 24 to maintain flatness of the capacitor stack 250, for example, for further processing. Alternatively, or in addition to, the optional channel 600 allows for a gripping device such as pliers to be slipped under the capacitor stack 250. In addition, precise alignment of the capacitor stack 250 is maintained by the alignment elements 500 when wrapping the capacitor stack 250.

Figure 13:
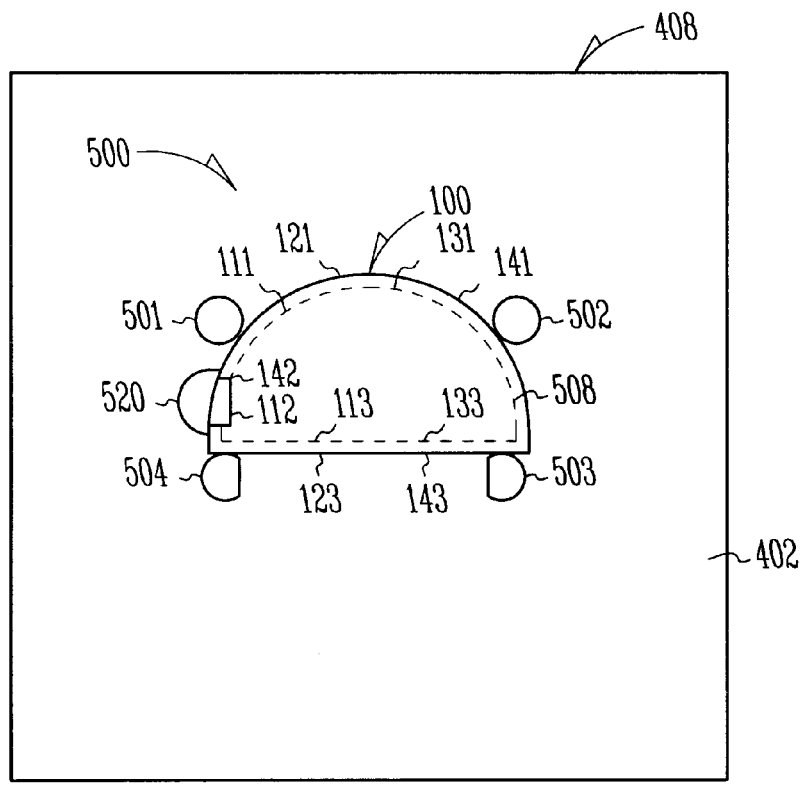
FIG. 13 is a top view of an anode stack aligned within an external alignment mechanism constructed in accordance with one embodiment.

FIG. 13 illustrates a top view of anode stack 100 within the anode external alignment mechanism 408, as described in FIG. 11A. To align the anode stack 100, each conductive layer 110, 114, 116, (FIG. 3) is placed in the recess 508. The anode separator 90 (FIG. 3) is placed over the conductive layers 110, 114, 116 and is aligned relative to the alignment elements 501, 502, 503, 504 by positioning the separator such that the first edge 141 and the flat edge 143 extend to contact each of the alignment elements 501, 502, 503, 504. The second recess 508 allows the anode separator 90 to be aligned relative to the conductive layers 110, 114, 116. The alignment elements 501, 502, 503, 504 concentrically align the separator 90 (FIG. 3) relative to the conductive layers 110, 114, 116 (FIG. 3).

In one embodiment, the anode external alignment mechanism 408 includes a recess 520. The recess 520 receives a portion of the edge clip 150 (FIG. 3) that extends beyond the anode stack 100 and allows the conductive layers 115 of the anode stack 100 to lay flat, one on top of the other within the anode external alignment mechanism 408. In one embodiment, the anode stack 100 is staked after being aligned in this manner.

Figure 14:
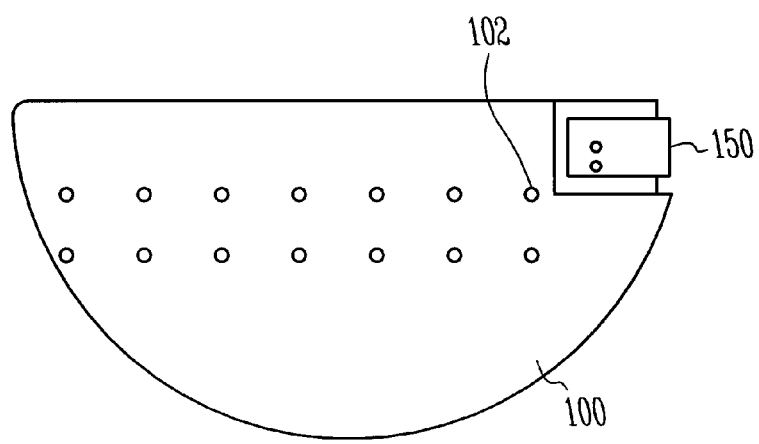
FIG. 14 is a top view of staking locations for a plurality of anode stacks constructed in accordance with one embodiment.

FIG. 14 illustrates one embodiment in which the anode stack 100 is removed from the anode external alignment mechanism 408 (FIG. 13) and staked so that the conductive layers of the anode stack 100 form an anode chip. In one embodiment, the anode stack is staked as described in co-pending U.S. patent application Ser. No. 09/706,518, filed on Nov. 3, 2000, entitled FLAT CAPACITOR HAVING STAKED FOILS AND EDGE-CONNECTED CONNECTION MEMBERS, and incorporated herein by reference in its entirety.

Figure 15:
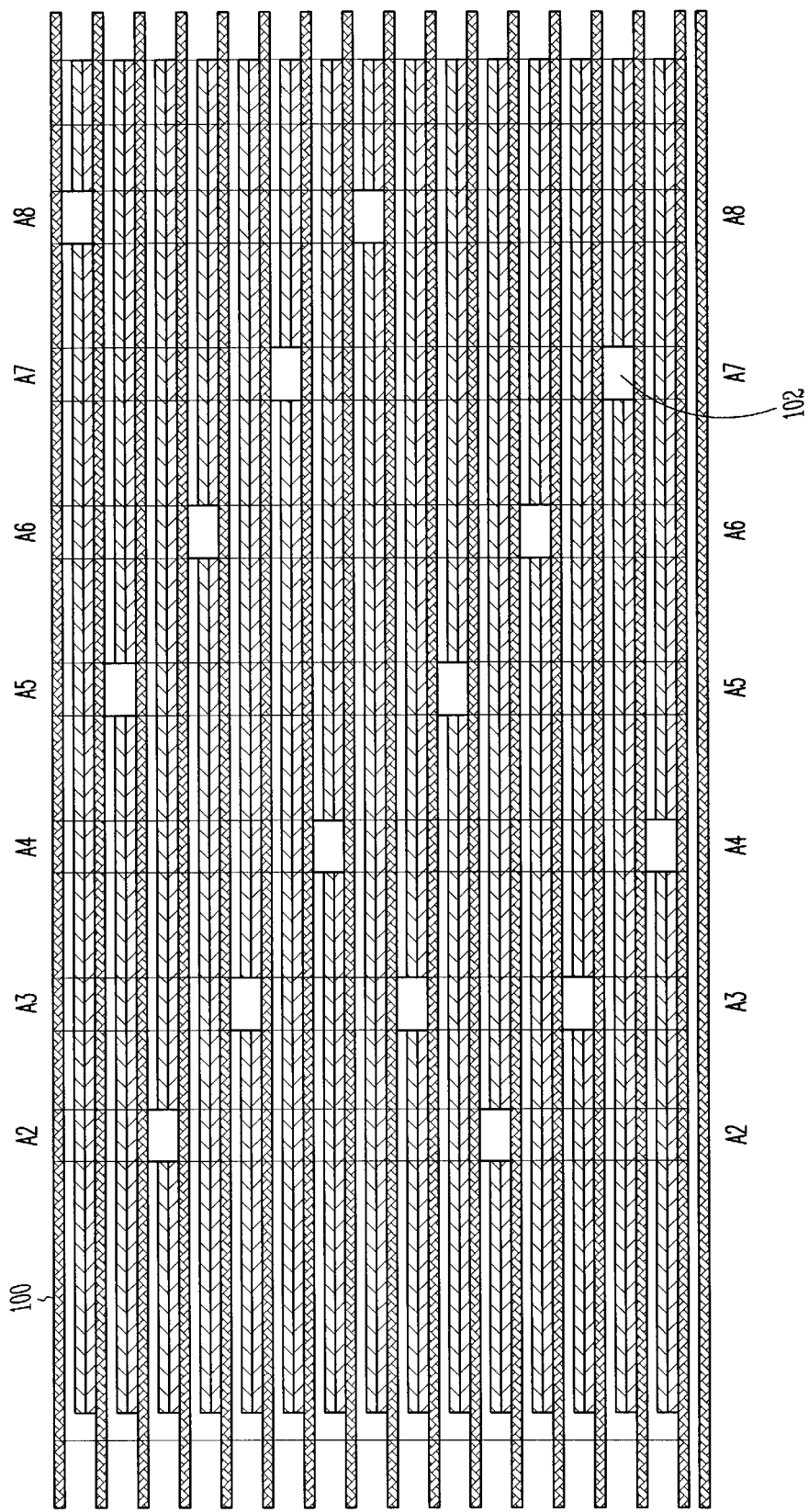
FIG. 15 is a cross-sectional view of the staking locations of FIG. 14.

In one embodiment, the staking locations 102 of the anode stacks 100 in the capacitor stack 24 (FIG. 1) are distributed so that anode stacks 100 in adjacent layers have staking locations that are offset from one another, as shown in FIG. 15 In one embodiment, the anode stack 100 is pressed after being staked to help reduce warpage and to reduce the overall height of the anode stack 100. In one embodiment, the anode stack 100 is pressed to a specific, predetermined height.

Figure 16:
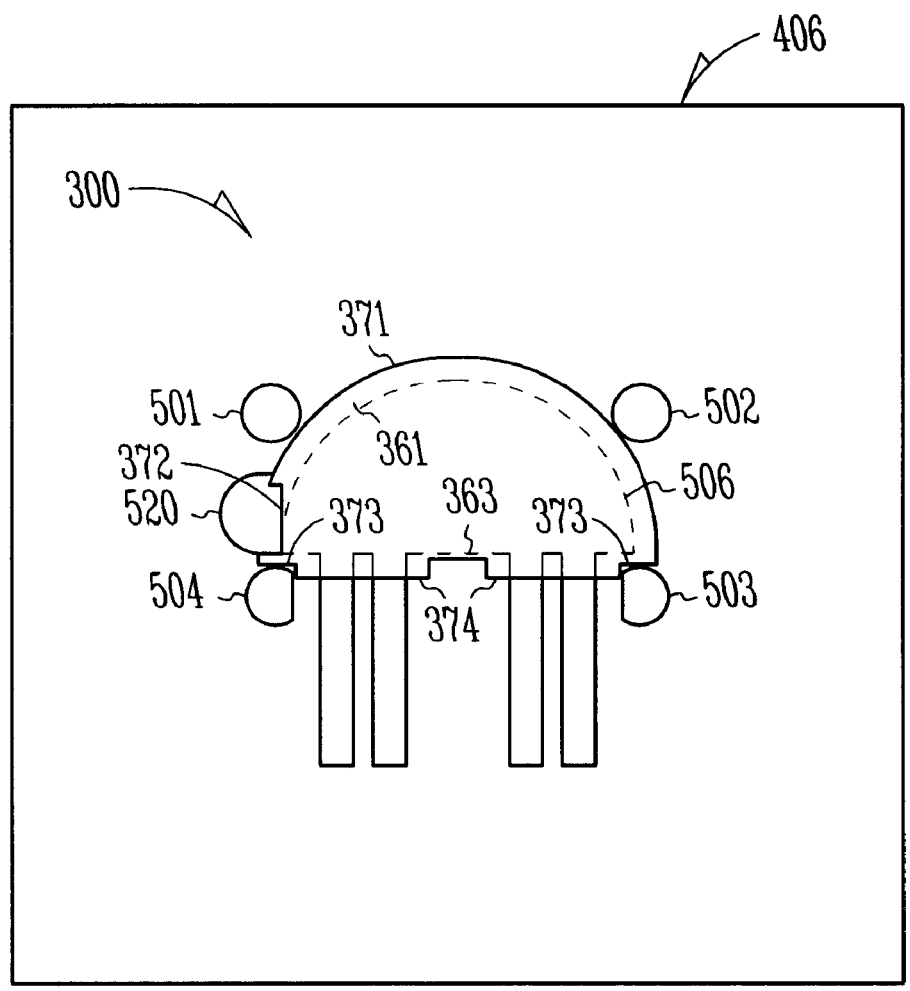
FIG. 16 is a top view of a cathode stack within an alignment mechanism constructed in accordance with one embodiment.

FIG. 16 illustrates a cathode stack 300 within a cathode external alignment mechanism 406. The same method is used to align the cathode conductive layer 60 and cathode separator layer 70 of the cathode stacks 50, 301, 302, 303 and 304, as was used to align the anode stack 100 (FIG. 13). The cathode conductive layer 60 is disposed within the recess 506, and the cathode separator layer 70 is aligned relative to the alignment elements 501, 502, 503, 504. Since the alignment elements 501, 502, 503, and 504 are placed in the same location for the anode external alignment mechanism 408, the cathode external alignment mechanism 406, and the external alignment mechanism 400 (FIG. 12), allows for the stacks 100, 300 to be better aligned to one another. This helps to reduce variances in alignment which may result from varying tolerance stack ups between layers of the assembly and the alignment mechanism used.

In one embodiment, the cathode separator layer 70 is aligned relative to the plurality of alignment elements 500 by stacking the cathode separator layer 70 so that edge 371 and flat edge 373 extend to contact each of the alignment elements 501, 502, 503, and 504. While aligned, the cathode separator layer 70 is coupled to the cathode conductive layer 60, for example, with adhesive. In one embodiment, each cathode stack 300 is pressed to help reduce warpage and thus to reduce the overall height of the capacitor stack 24 (FIG. 1).

Figure 17:
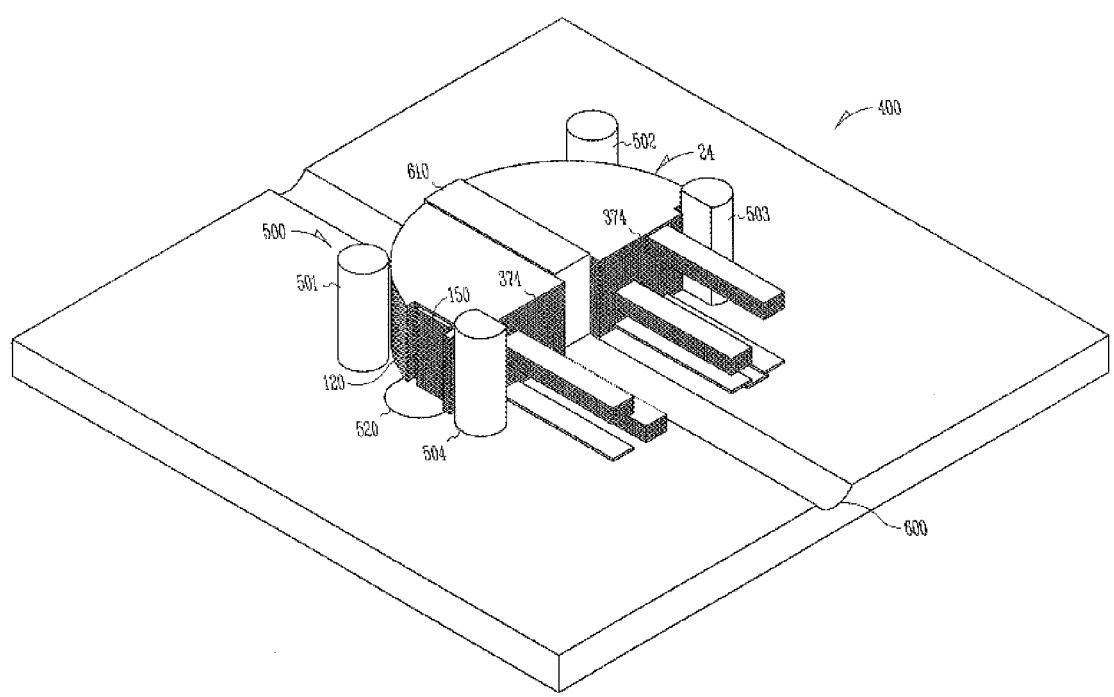
FIG. 17 is a perspective view of a cathode stack in an alignment mechanism constructed in accordance with one embodiment.

FIG. 17 illustrates a capacitor stack 24 within an external alignment mechanism 400. In this embodiment, the capacitor stack 24 includes a plurality of layers 120, including anode stacks 100 (FIG. 3), and cathode stacks 300 (such as cathode stacks 50, 301–304 in FIGS. 6–10), which were each individually aligned with the anode external alignment mechanism 408 and the cathode external alignment mechanism 406, respectively. The anode stacks 100 and the cathode stacks 50, 301–304 are aligned relative to the alignment elements 500 using one or more outer edges of the cathode separators 70 (FIGS. 6–10) and one or more outer edges of the anode separators 90 (FIG. 3). In one embodiment, capacitor stack 24 includes separators 200 (FIG. 5) and the alignment elements 501, 502, 503, 504 further align each separator 200 relative to the anode stacks 100 and the capacitor stacks 300 using an outer edge of the separator 200 (FIG. 5). In some embodiments, separators 200 are omitted and capacitor stack 24 is aligned relative to the alignment elements 500 using only one or more outer edges of the cathode separators 70 (FIGS. 6–10) and one or more outer edges of the anode separators 90 (FIG. 3).

In one embodiment, a fastener 610 is wrapped around a portion of the stack 24 to retain the alignment of the layers 120 relative to one another. In one embodiment, fastener 610 comprises tape that is wrapped around a central portion of the capacitor stack 24. Optionally, the capacitor stack 24 is then clamped and annealed, with or without the fastener 610. The channel 600 optionally allows for a tool and/or a robot to be disposed under the stack 24.

In some embodiments, the anode stack 100 and the cathode stacks 50, 301–304 are aligned relative to one another within the case 20, instead of using the external alignment mechanism 400, and then are coupled to one another in the aligned position. For instance, an outer edge of a separator of the anode stack 100 (FIG. 3) and an outer edge of a separator of the cathode stacks 50, 301–304 (FIGS. 6–10) would contact an interior surface of the case 20, and would be aligned therein.

Among other advantages, one or more embodiments of the alignment mechanism described provide for a capacitor making efficient use of space within the case, permit increased anodic surface area, and increased capacitance for a capacitor of a given set of dimensions. Variation in the outer dimensions of one capacitor stack to another capacitor stack is reduced because each is formed within alignment elements positioned the same manner. Dimensional variations in the capacitor stack resulting from variation in the reference points from case to case or alignment apparatus to alignment apparatus are eliminated. This provides improved dimensional consistency in production and allows for reduced tolerances between the capacitor stack and the capacitor case. This allows for more efficient use of space internal to the capacitor case. Each first electrode stack, second electrode stack and each separator is aligned relative to the position of the alignment elements.

Moreover, the capacitor stack structure described above provides for greater anodic surface area since, by aligning to the separator, the anode surface area is optimized by not having to provide extraneous alignment notches or other alignment features on the anode foil itself which decrease the anode surface area.

Since the external alignment mechanism is exterior to the case, better visual observation of the alignment of each electrode stack and separator is provided. Furthermore, multiple points are used to make the alignment, reducing the effect of the tolerance stack up between the conductive layer or separator being aligned and the alignment element at any one position. This also facilitates for alignment of components which during certain steps in the manufacturing process have portions which extend beyond the dimensions defined by the case and are later formed to fit within the case.

In some embodiments, the edges of the cathodes and anodes described above are generally co-extensive or aligned with each other within stack 24. In other embodiments, capacitor stack 24 includes anode and cathode layers having at least partially offset edges.

Figure 18:
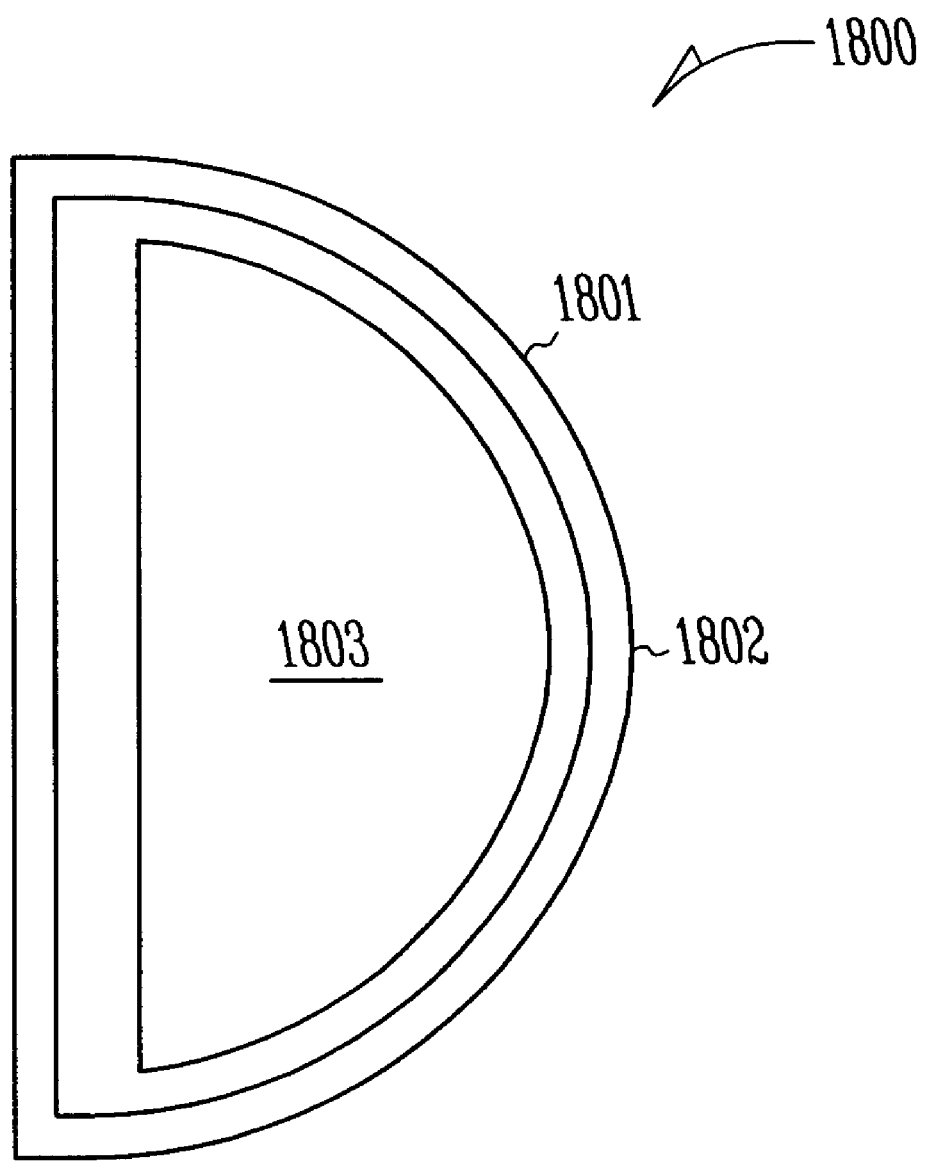
FIG. 18 is a top view of a capacitor stack according to one embodiment.

FIG. 18 shows a planar view of a cathode stack 1800 according to one embodiment. The capacitor stack 1800 includes an anode layer 1801, a separator 1802, and a cathode layer 1803 that are configured in a layered structure analogous to capacitor stack 24 described above. The bottom surface in the figure is the anode layer, and the top surface is the cathode layer with the paper separator interposed therebetween. The separator includes two paper separators impregnated with an electrolyte that conducts current between the anode and cathode layers.

Some cutting processes used to make anode and cathode foil layers can produce burrs on the foils that can result in a short circuit if a burr on an anode layer edge portion makes contact with an adjacent cathode layer or vice-versa. When the dimensions of the cathode and anode layers are the same so that the edges of each layer are aligned, a burr on a cathode layer edge portion can then contact a burr on an anode layer edge portion. Burrs on overlapping edge portions of the anode and cathode layers may then make contact and cause a short circuit by traversing only half of the thickness of the paper separator between the two layers.

Accordingly, in one embodiment, the capacitor stack is constructed with layers having edge portions that are offset from one another. In one embodiment, this is done by having a cathode layer with a different dimension than the anode layer so that portions of their edges are offset in the layered structure (i.e., either the anode layer or the cathode layer is smaller than the other). The anode and cathode layers may be of the same general shape, for example, but of different surface areas so that the perimeter of one layer is circumscribed by the perimeter of the other layer.

The capacitance of an electrolytic capacitor results from the charge separation between the electrolyte and the anode layer so that altering the surface area of the cathode layer does not appreciably affect the capacitance of the device. Such an arrangement is shown in FIG. 18 where the cathode layer 1803 is of the same general shape as the anode layer 1801 but with a smaller surface area such that the edge portions of the cathode layer are inwardly offset from the anode layer edges. In this structure, only an edge burr on the cathode layer that traverses the entire thickness of the paper separator can produce a short circuit. This is in contrast to the case where the edge portions of the two layers are aligned rather than being offset. Offsetting the edge portions results in a greater tolerance for edge burrs and allows a less constrained manufacturing process.

Figure 19:
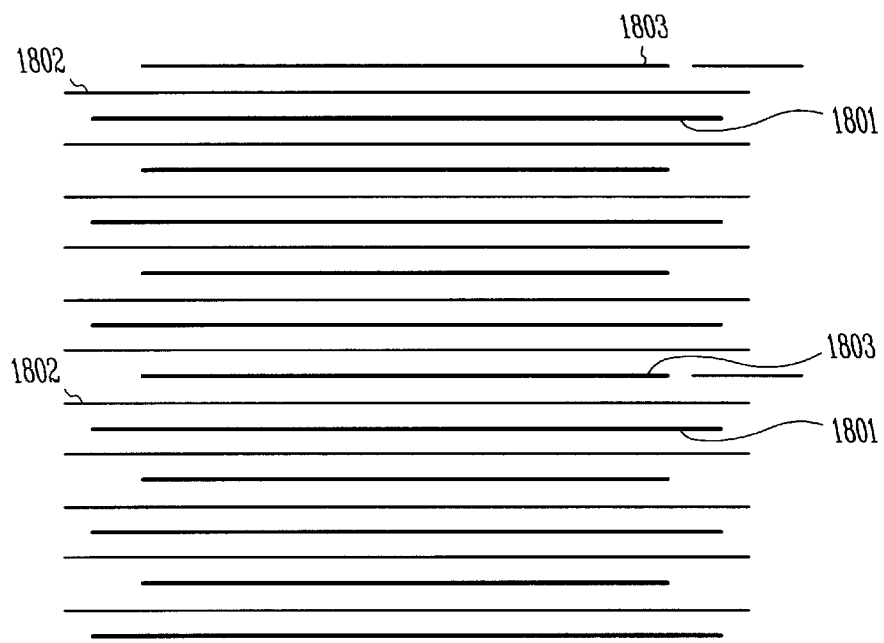
FIG. 19 is a side schematic view of the capacitor stack of FIG. 18.

FIG. 19 shows a cross-sectional schematic of capacitor stack 1800. The capacitor is made up of a plurality of capacitive elements that are stacked on one another with each capacitive element being a layered structure capacitor such as shown in FIG. 18. The anode layers 1801 are stacked on cathode layers 1803 in alternate fashion with paper separator 1802 interposed between each anode layer and each cathode layer.

Figure 20:
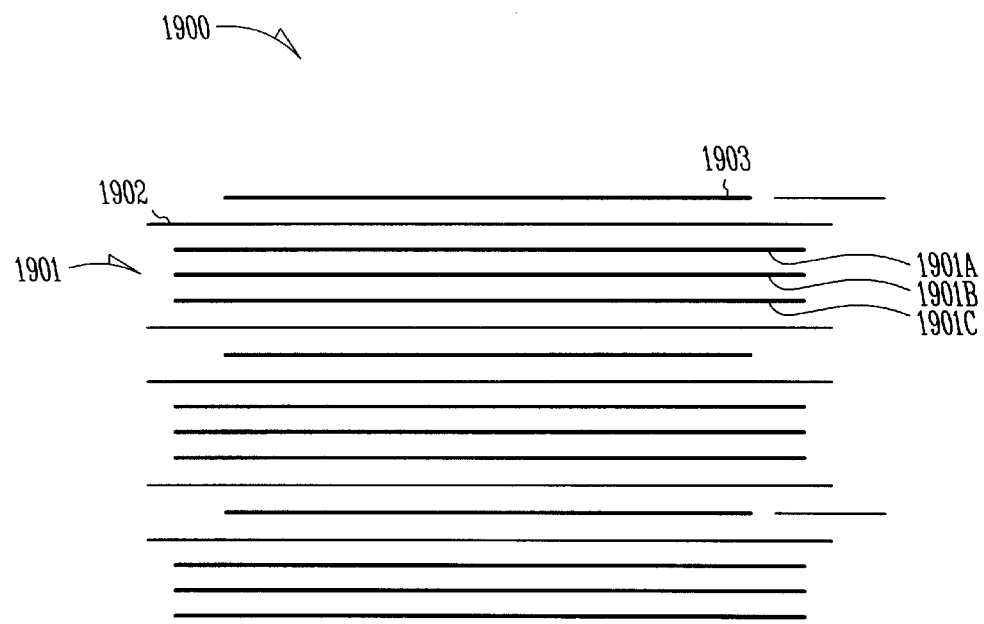
FIG. 20 is a side schematic view of a capacitor stack according to one embodiment.

FIG. 20 shows a capacitor stack 2000 according to one embodiment. Capacitor stack 2000 includes multiple porous anode layers 1901. The multiple layers result in a greater surface area exposed to the liquid electrolyte and a greater capacitance for each element. Three anode layers 1901a–1901c are shown in the figure which are stacked together with a paper separator 1902 and cathode layer 1903 on each side of the stack. The liquid electrolyte flows through perforations in the anode layers to reach the oxide layers of each layer. The edge portions of each cathode layer 1903 are inwardly offset from the edge portions of each overlying and underlying anode layer 1901.

In one embodiment, the offset structure described above can be incorporated into a cylindrical capacitor. For instance, the anode and cathode layers are cut from a sheet in a desired width and length. The cathode layer is made narrower than the anode layer so that the edges of the cathode layer are inwardly offset from the anode layer edges. The cylinder configuration is then produced by rolling the layers into concentric anode and cathode layers that are separated by electrolyte.

Offsetting of anode layer and cathode layer edge portions may be accomplished by using a variety of differently shaped and/or dimensioned cathode or anode layers.

In some embodiments, the cathode layer reduction ratio relative to the anode layer is limited. The electrical equivalent circuit of an electrolytic capacitor is the series connection of an anodic capacitance due to the charge separation that occurs between the anode layer and the electrolyte across the dielectric layer, an equivalent series resistance of the capacitor or ESR, and a cathodic capacitance due to the charge separation that occurs between the cathode layer and the electrolyte. When a capacitor is charged to its rated voltage, the voltage is divided and dropped across between the cathodic capacitance Cc and the anodic capacitance Ca. Since the charge stored on cathode layer Qc must equal the charge stored on the anode layer Qa, then:

Qa=Qc

CcVc=CaVa where Vc is the voltage dropped across the cathodic capacitance and Va is the voltage dropped across the anodic capacitance.

The voltage Vc is thus inversely proportional to the cathodic capacitance. The cathodic capacitance should be large enough so that only a small voltage drop occurs across it when a voltage is applied to the capacitor, with most of an applied voltage being dropped across the anodic capacitance. If the cathode layer is made small enough relative to the anode layer, the cathode layer's capacitance may be reduced to such an extent that when the capacitor's rated voltage is applied an overvoltage condition occurs at the cathode layer with the creation of oxide and evolution of hydrogen gas.

Accordingly, in one embodiment the cathode layer is limited to the degree of decrease in surface area relative to the anode layer. In one embodiment, the cathode layer is kept to a size that keeps the overvoltage at tolerable levels when a rated voltage is applied to the capacitor. Such a minimum size for a cathode layer will vary, of course, with the capacitor's geometry and its rated operating voltage, but the size limit can easily be determined empirically.

In one embodiment, for example, a flat capacitors used in implantable defibrillators and designed to operate at a rated voltage of 400 volts, includes a ratio of the cathode layer surface area to the anode layer surface area of approximately 0.75 or greater. In some embodiments, the ratio is approximately 0.75 to approximately 0.93. In some embodiments, the ratio is approximately 0.93.

In some embodiments, capacitor stack 24 includes a uniform level of anode foils in each anode stack 200. In other embodiments, the number of anode foils varies.

Figure 21:
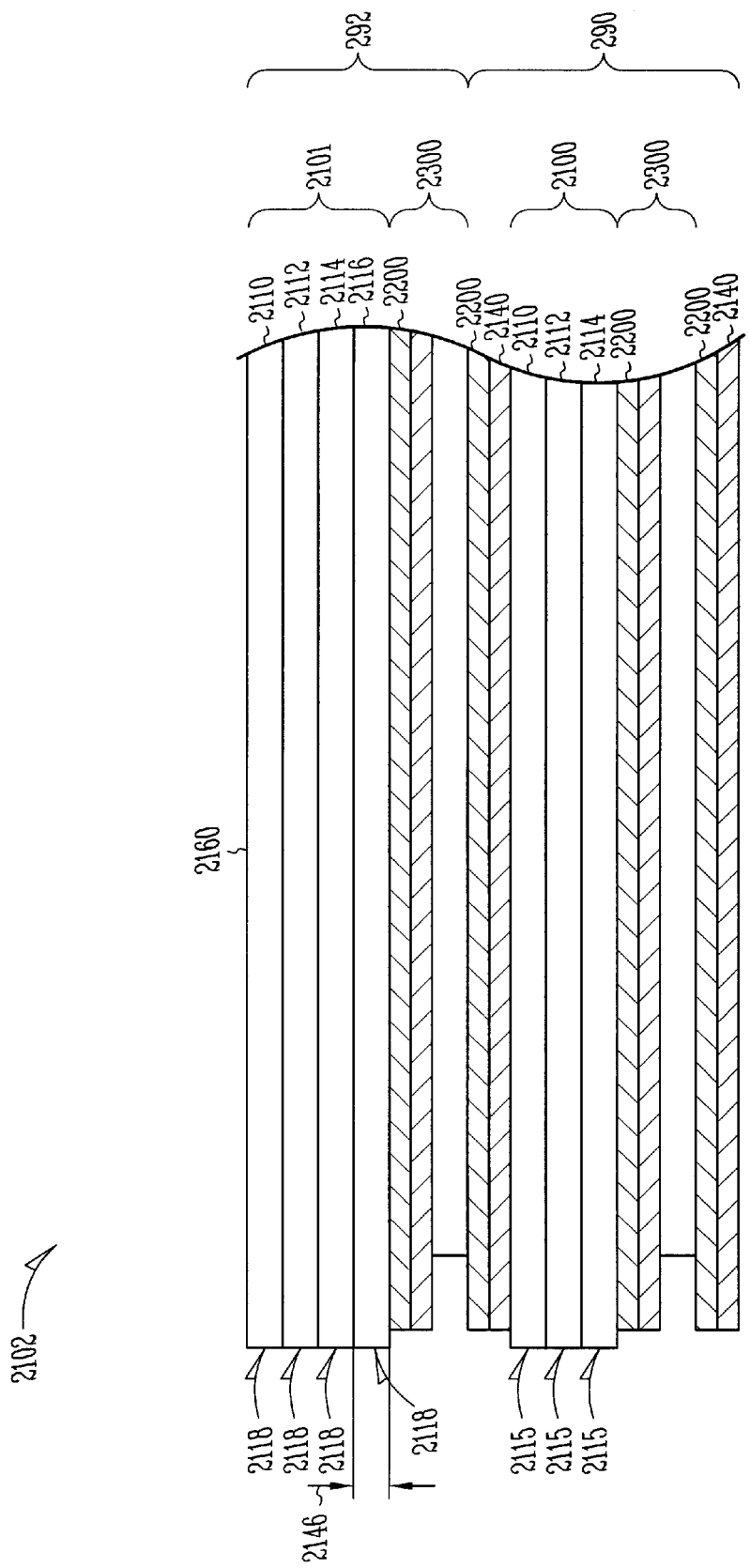
FIG. 21 is a cross-sectional view of a capacitor stack constructed in accordance with one embodiment.

For instance, FIG. 21 illustrates a cross-section of a capacitor stack 2100 according to one embodiment. One example of mixed anode stacks 2102 is shown, which includes an anode stack 2100 and a modified anode stack 2101. The anode stack 2100 includes at least one conductive layer 2115 having a height 2146. The modified anode stack 2101 includes a plurality of conductive layers 2118 such that the modified anode stack 2101 includes at least one more conductive layer than included in the anode stack 2100. The anode stack 2100 and the modified anode stack 2101 differ in the quantity of conductive layers in each. In addition, the anode stack 2100 and the modified anode stack 2101 differ in the total surface area of each.

Figure 23:
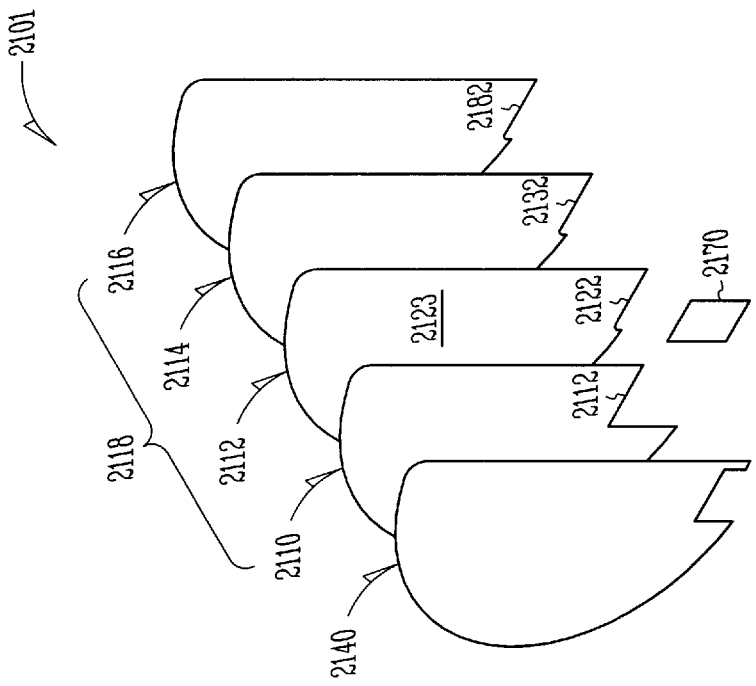
FIG. 23 is an exploded view of a modified anode stack constructed in accordance with one embodiment.
Figure 22:
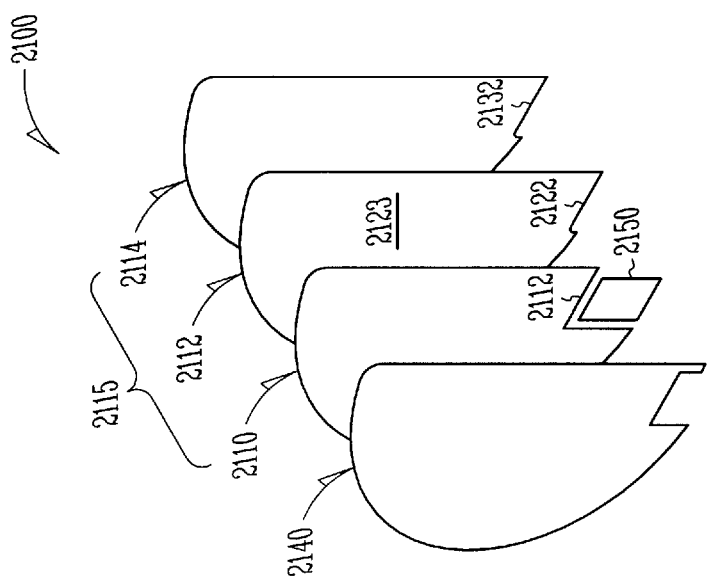
FIG. 22 is an exploded view of an anode stack constructed in accordance with one embodiment.

The anode stack 2100, also shown in FIG. 22 includes a first conductive element 2110, a second conductive element 2112, and a third conductive element 2114, and an anode separator 2140. In one embodiment, as shown in FIG. 23, a modified anode stack 2101 includes a first conductive element 2110, a second conductive element 2112, a third conductive element 2114, and a fourth conductive element 2116, and an anode separator 2140, where the modified anode stack 2101 includes at least one more conductive element than the anode stack 2100. In another option, the modified anode stack 2101 includes one or more less conductive elements than the anode stack 2100.

Figure 24:
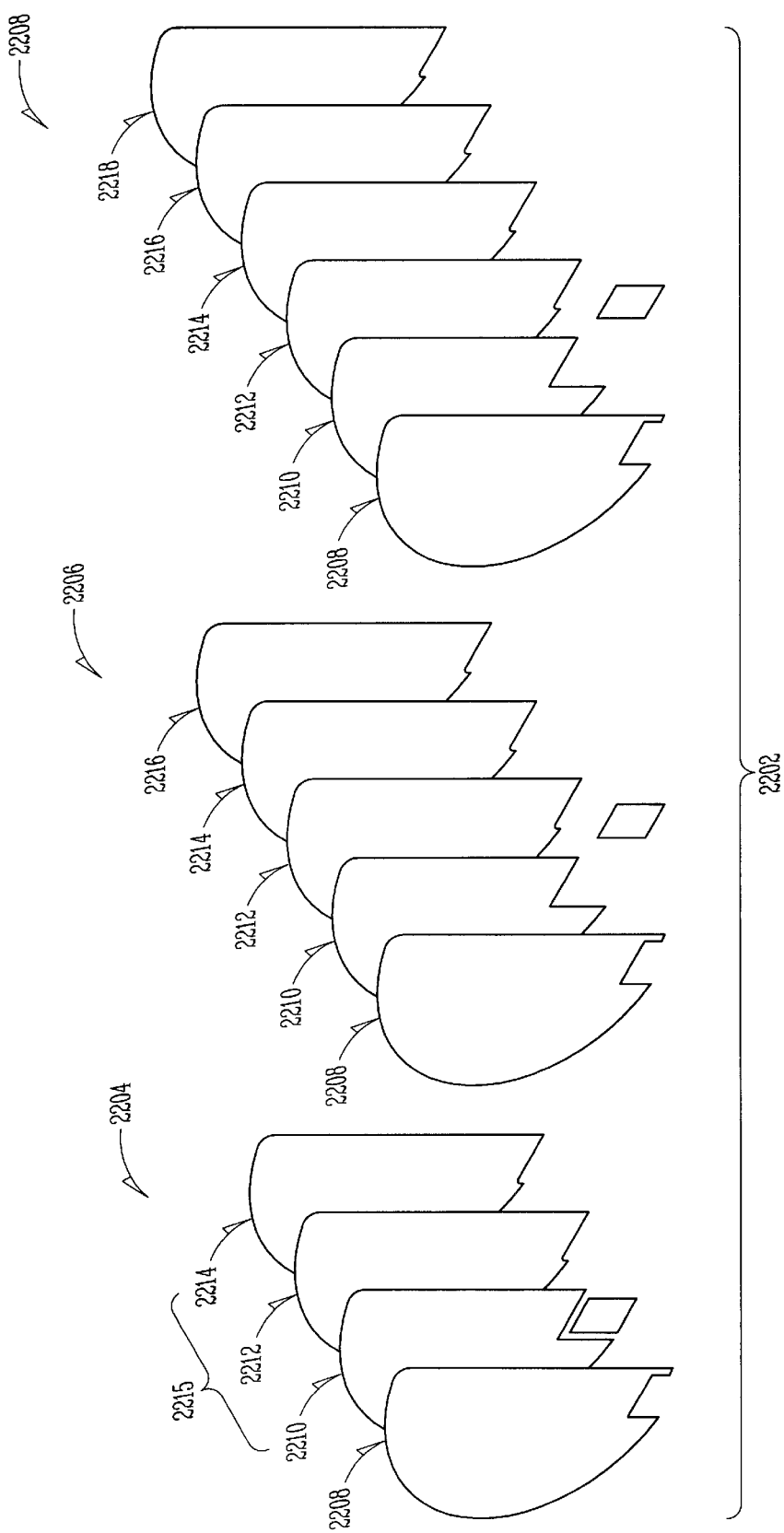
FIG. 24 is an exploded view of a mixed anode stack constructed in accordance with one embodiment.

FIG. 24 illustrates another example of mixed anode stacks 2202, which includes a first anode stack 2204, a second anode stack 2206, and a third anode stack 2208. The first anode stack 2204 has a plurality of conductive layers 2215 including a first conductive element 2210, a second conductive element 2212, and a third conductive element 2214. In one option, the second anode stack 2206 includes a first conductive element 2210, a second conductive element 2212, a third conductive element 2214, and a fourth conductive element 2216. The third anode stack 2208 includes a first conductive element 2210, a second conductive element 2212, a third conductive element 2214, a fourth conductive element 2216, and a fifth conductive element 2218, where the second and third anode stacks 2206, 2208 include a different number of conductive elements than the first anode stack 2204. In another option, the modified anode stack 2201 includes one or more less conductive elements than the anode stack 2200.

In one embodiment, the first anode stack 2204 has a first surface area, and the second anode stack 2206 has a second surface area, and the first surface area is different than the second surface area, for example the second surface area is greater than the first surface area. In a further option, the first anode stack 2204 has a first surface area, the second anode stack 2206 has a second surface area, and the third anode stack 2208 has a third surface area. The third surface area is different than the first surface area and/or the second surface area, for example the third surface area is greater than the first surface area and/or the second surface area. The surface areas can be modified by modifying the surface of the conductive elements, for example, by etching. It should be noted that additional combinations of conductive layers and/or surface areas are contemplated and are considered within the scope of one or more embodiments of the present invention.

Figure 25:
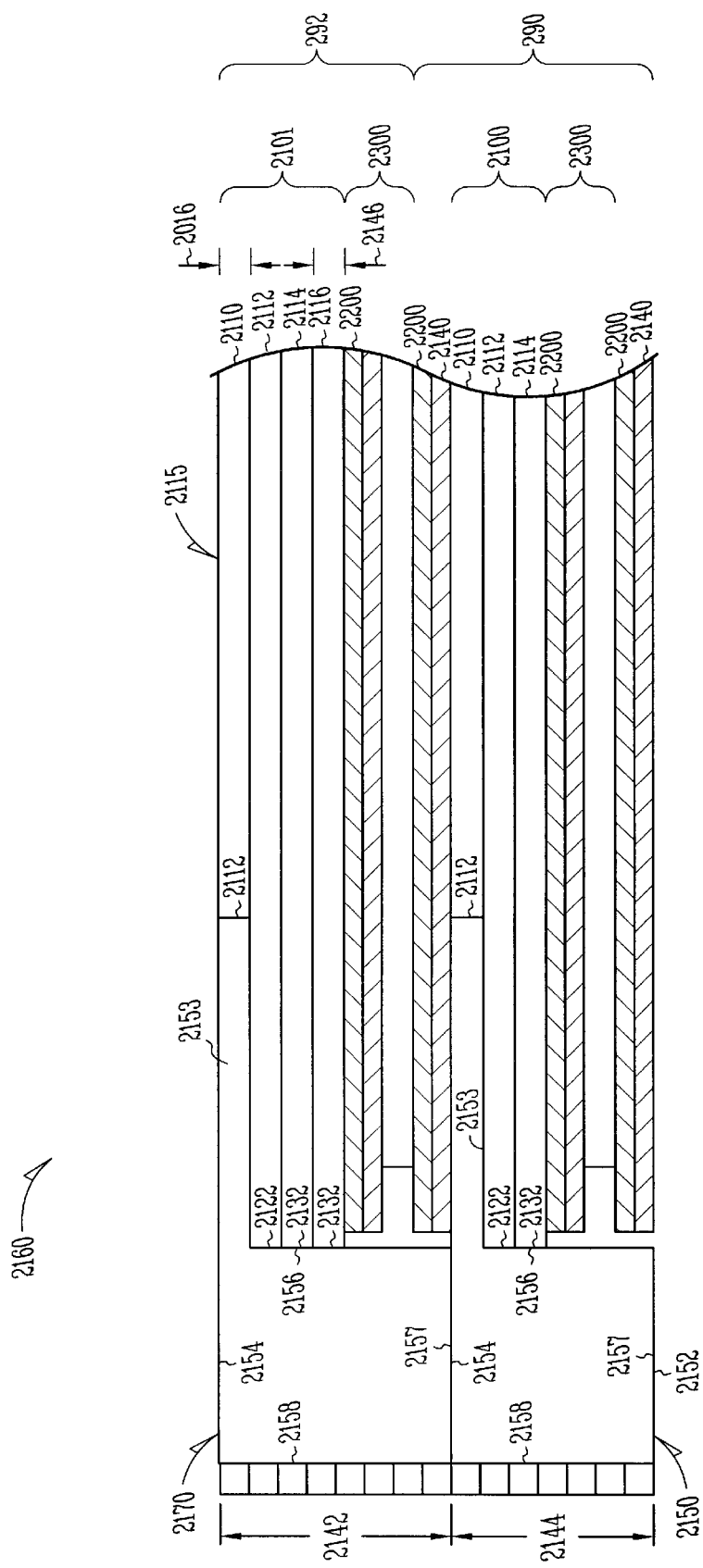
FIG. 25 is a cross-sectional view of a capacitor stack constructed in accordance with one embodiment.

Referring to FIG. 25 the anode stack 2100 is coupled with the modified anode stack 2101, where there are a variety of ways to couple the modified anode stack 2101 with the anode stack 2100. In one example, the stack 2160 includes an edge clip 2150 and a modified edge clip 2170, which interconnect the modified anode stack 2101 with the anode stack 2100. The modified edge clip 2170, which is coupled with the modified anode stack 2101, has a height 2142 that is extended for a slightly higher height of the modified anode stack 2101. The edge clip 2150 coupled with the anode stack 2100 has a height 2144 suitable for use with the anode stack 2100. The edge clips 2150, 2170 permit taller anode stacks to be reliably combined. The edge clips 2150, 2170 are anodic and are optionally used to increase anodic surface area of the conductive layers 2115 as the edge clips 2150, 2170 require little space within the capacitor stack 2160. The composition of cells 290 and modified cells 292 as further discussed below, can be modified without requiring changes to other components in the capacitor stack 2160 resulting in greater design flexibility.

Referring again to FIG. 21, the capacitor stack 2160 includes at least one cell 290, where each cell 290 includes an anode stack 2100, an anode separator 2140, a cathode stack 2300, and a cathode separator 2200. In addition, the capacitor stack 2160 includes at least one modified cell 292, where each modified cell 292 includes a modified anode stack 2101, an anode separator 2140, a cathode stack 2300, and a cathode separator 2200. In one option, the cathode stack 2300 and the cathode separator 2200 are substantially the same as included in the cell 290 and the modified cell 292, such that the difference in height between the anode stack 2100 and the modified anode stack 2101 is due to the increase in height of the modified anode stack 2101 resulting from the modified anode stack 2101 having a greater number of conductive layers 2115 than included in the anode stack 2100. In another option, the modified anode stack 2101 of the modified cell 292 has fewer conductive layers 2115 than the anode stack 2100.

In one embodiment, a plurality of modified cells 292 are distributed throughout the capacitor stack 2160 in a manner to optimize use of existing cathodic area. In one example, the capacitor stack 2160 includes fifteen cells, where at otherwise would be every fifth cell 290, a modified cell 292 is disposed instead. Since the modified anode stack 2101 of the modified cell 292 includes at least one more conductive layer than the anode stack 2100, the resulting example of capacitor stack 2160 includes at least three additional conductive anode layers within the case 20 (FIG. 1), without a substantial increase in the height of the components therein. For instance, for the capacitor stack 2160, instead of adding an additional anode stack 2100, which would have a height of three conductive layers 2115 (FIG. 21), and the height of an anode separator 2140 (FIG. 21), and the height of a separator 2200, and the height of a cathode stack and an additional separator, only the height of the additional conductive layers 2115 in the modified anode stack 2101 is added to the height of the capacitor stack 2160.

In other embodiments the modified anode stack 2101 contains one, two, three, four, five, six or more conductive layers 2115 than is included in each anode stack 2100. Alternatively, more than one type of modified anode stack 2101 is included with the capacitor stack 2160.

Referring again to FIG. 25, a stack 2160 is shown which includes cell 290, and modified cell 292. An edge clip 2150 is adjacent the edge clip 2170 of an adjacent modified cell 292. The edge clip 2150 is coupled to adjacent modified edge clip 2170. For example, the edge clip 2150 is welded to the modified edge clip 2170. Where a plurality of cells 290 and modified cells 292 are provided, a plurality of edge clips 2150, 2170 are also provided. The plurality of edge clips 2150, 2170 stack one on the other such that the bottom surface 2157 of an edge clip 2150 or modified edge clip 2170 contacts the upper surface 2154 of an adjacent modified edge clip 2170, or edge clip 2150. The stacked edge clips 2150, 2170 provide a larger contact surface 2158 increasing ease of attachment thereto. Each anode stack 2100 and modified anode stack 2101 remain essentially flat and do not require the ductility required of other designs to make an electrical connection. The stacked edge clips 2150, 2170 provide for layer designs having higher stack composed of less ductile materials previously used, and further provide for interconnections in less space.

In one option, an upper portion 2153 of the edge clip 2150 or modified edge clip 2170 is positioned within a clearance area 2112 of the first conductive element 2110. A side portion 2152 of the edge clip 2150 extends along the edges 2122, 2132 of the second 2112 and third 2114 conductive elements, and extends along the edges of separators 2200, and further along the edge of the anode separator 2140 of an adjacent modified anode stack 2101. The edge clip 2150 remains separate from the cathode stack 2300. The side portion 2152 of the modified edge clip 2170 extends along the edges 2122, 2132, 2182 of the second 2112, third 2114, and fourth 2116 conductive elements. The side portion 2152 also extends along the edges of separators 2200, as well as along the edge of the anode separator 2140 of an adjacent anode stack 2100 or modified anode stack 2101. The edge clip 2170 remains separate from the cathode stack 2300.

In one or more embodiments, edge clips are utilized such as one or more connection members described in co-pending U.S. patent application Ser. No. 09/706,518, filed on Nov. 3, 2000, entitled FLAT CAPACITOR HAVING STAKED FOILS AND EDGE-CONNECTED CONNECTION MEMBERS, and cited above.

In one embodiment, a method is also provided, the method involving aligning an anode stack, including aligning at least one conductive layer having a surface and an edge, and aligning a first separator between the anode stack and a modified anode stack. The method further includes aligning at least one modified anode stack with the anode stack, which includes aligning a plurality of conductive layers, wherein the plurality of conductive layers includes at least one more conductive layer than included in the anode stack and one of the plurality of conductive layers having a surface and an edge, and electrically coupling the anode stack with the modified anode stack.

Several variations for the method are as follows. The method further including welding an edge clip to the modified anode stack. In another option, the method further includes aligning a first modified anode stack and a second modified anode stack, each having a plurality of conductive layers. In yet another option, the method further includes stacking a first number of layers to form the first modified anode stack, and stacking a second number of layers to form the second modified anode stack, and the first number of layers is different than the second number of layers. In yet another option, the method further includes aligning a second separator between the first modified anode stack and the second modified anode stack.

Advantageously, the mixed-anode capacitor stacks described above allow for a reduction in the volume, thickness, and the mass of the stack without a reduction in the deliverable energy, which provides for a smaller overall device size. This results in increased patient comfort, and reduces tissue erosion surrounding the implantable device. In addition, reducing the size of the capacitor allows for other critical component sizes to be increased, for example, the battery, or for other components to be added. A further benefit is that anodic surface area is increased without requiring additional cathodic area to support the added anode conductive layers. This allows a boost in capacitance with a minimal increase in thickness of the capacitor. In empirical studies, capacitors that included the modified anode stack showed capacitance values of 186 $\mu$F, 185 $\mu$F, and 186 $\mu$F, compared to standard devices without the modified anode stack which had capacitance values of 172 $\mu$F, 172 $\mu$F, and 173 $\mu$F.

Referring again to FIG. 17, once stack 24 is stacked as shown, the anode and cathode layers are interconnected. In one embodiment, the cathode layers are constructed and connected as described following.

Figure 26:
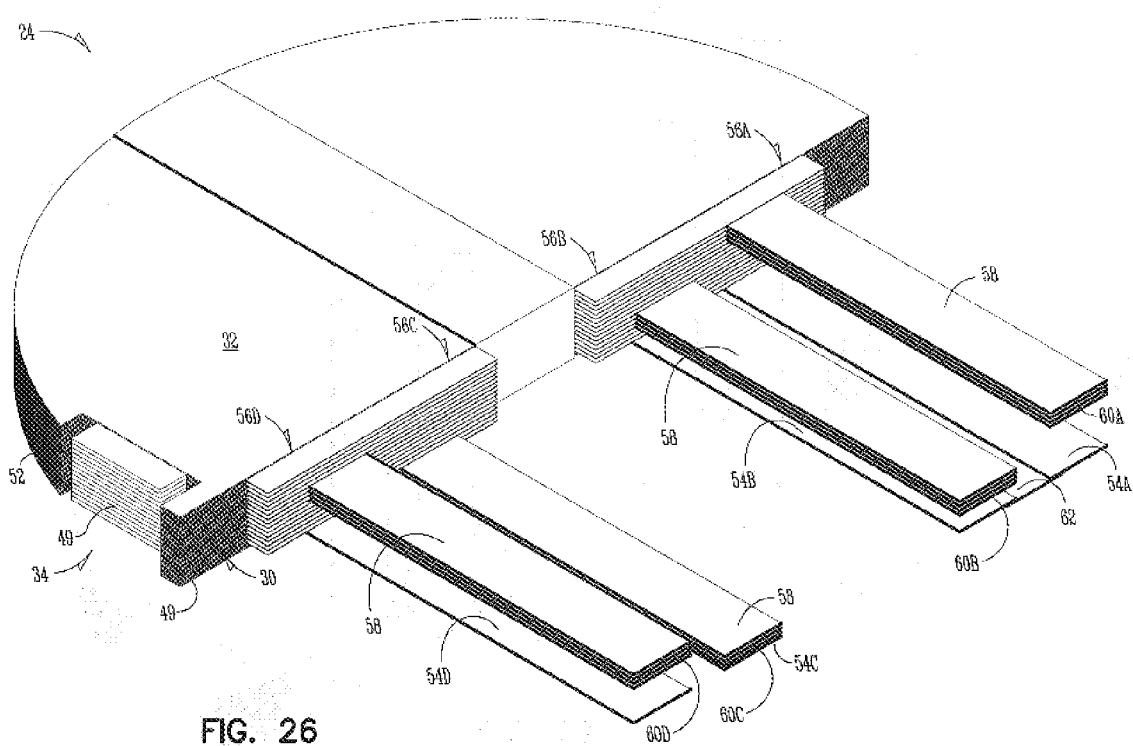
FIG. 26 is a perspective view of a capacitor stack according to one embodiment.

FIG. 26 shows further details of capacitor stack 24 according to one embodiment of the present invention. As described above, the cathode layers 300 include base foil layer 50 and a plurality of secondary foil layers 301–304, here denoted generally as layers 52. The base layer has a plurality of base tabs 54a–54d including a first base tab 54a in a first tab position 56a, a second base tab 54b in a second tab position 56b, a third base tab 54c in a third tab position 56c, and a fourth base tab 54d in a fourth tab position 56d. The present description is an example. Other embodiments include more tabs and less tabs with varying numbers of tab positions. Each tab 54a–54d is electrically coupled to the other tabs 54a–54d through base layer 50, which includes at least one tab at each tab location. Each secondary layer 52 has at least one extension member or leg 60a–60d positioned to overlay, be co-extensive with, or match with one of the plurality of tab positions 56a–56c.

In this embodiment, the cathode layers are positioned to include a first layer group 60a, a second layer group 60b, a third layer group 60c and a fourth layer group 60d. Other embodiments have more layers or less layers. The layer groups are in electrical contact with each other, but spaced apart from the anode tabs 49 to allow separate connection of anode layers 46 without shorting. The layer groups electrically connect to an external cathode connection or cathode lead 62 which provides an external electrical connection to the case.

Each group of extension members 60a–60c is positioned to overlay one of a plurality of tab positions 56a–56d. The plurality of secondary layers are portioned into the plurality of the layer groups. The matching tabs of each layer group are located in the same position. For example, each of the matching tabs 60a of first layer group 60a are located in first tab position 56a so that the matching tabs 60a overlay first base tab 54a, which is also in first tab position 56a. In other words, from a top view perspective, tabs 60a are commonly positioned or co-extensive with base tab 54a. Secondary layers in each layer group are shown as located in adjacent layers. Alternatively, the layer groups may comprise secondary layers from non-adjacent layers.

Figure 27:
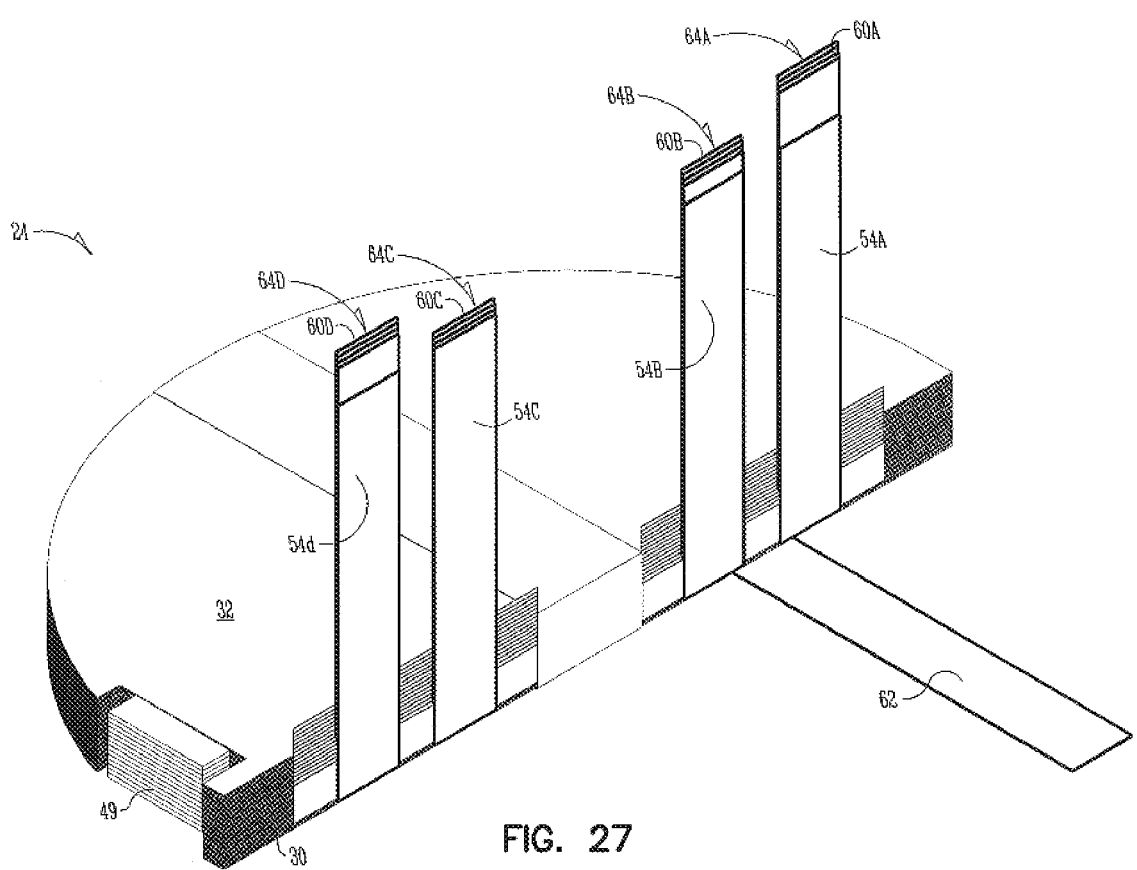
FIG. 27 is a perspective view of the capacitor stack of FIG. 26.

FIG. 27 shows another view of the capacitor stack 24 having matching tabs of each secondary layer group 60 folded and welded to the corresponding tab 54 of the base layer, forming a plurality of tab groups 64. The tab groups 64 electrically connect to an external cathode connection or cathode lead 62 which provides an external electrical connection to the case.

The cathode layers 44 include a first tab group 64a, a second tab group 64b, a third tab group 64c and a fourth tab group 64d. The tab groups 64 are also in electrical contact with each other, but spaced apart from the anode tabs 49 to allow separate connection from the anode layers 46 without shorting. The tab groups 64 are electrically connected to the capacitor case 20 or alternatively may be insulated from the case 20.

Figure 28:
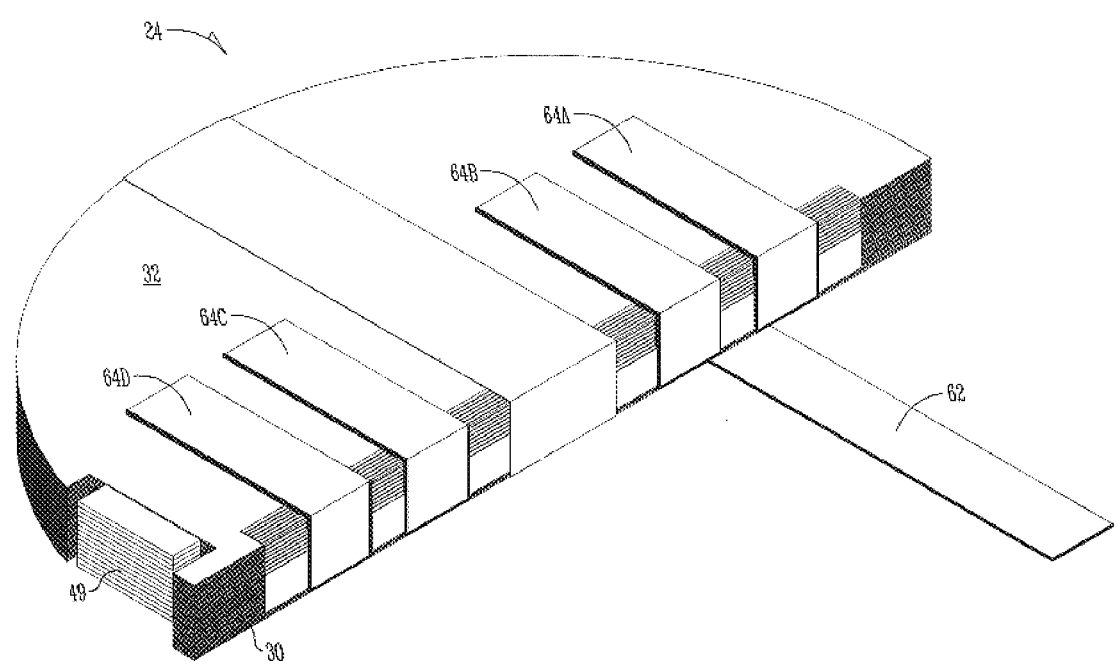
FIG. 28 is a perspective view of the capacitor stack of FIG. 26 with a plurality of tab groups positioned on the top surface of the capacitor stack.

FIG. 28 shows another view of capacitor stack 24 showing tab groups 64 folded into position on the top surface 32 of capacitor stack 24. The tab groups have a reduced thickness and are folded onto the top of the stack and taped. Alternatively, the tab groups are cut just beyond the weld and taped against the face 30 of the stack. Each tab group 64 has a thickness that is less than the sum of the base layer and all the secondary layers.

The thickness of the tab groups are approximately equal to or less than space 40 as previously shown in FIG. 1. As noted above, in some embodiments, space 40 is merely a line-to-line interference fit. The present cathode structure provides that the cathode interconnections fit within the limited room available. Alternatively, the tab groups are located in space 40 between the face 30 of stack 24 and the case 20 or base 26.

In this embodiment, base layer 50 has four base tabs 54a–54d and each secondary layer 52 has at least one tab 58 that matches one of the base tabs 54a–54d. The base tabs and matching tabs may be staked to the foil layer or the tabs may be integral with the foil layer. The layers 50, 52 may have two or more tabs. The base tabs are shown with four tabs and the secondary tabs are shown with one tab. In some embodiments, the secondary layers include two or more tabs to create redundancy.

The embodiment described above show the base layer and secondary layer as cathode layers. However, the anode layers may also be arranged in a similar fashion. The anode layers may include a base layer with base tabs and secondary layers with matching tabs either alternatively or in addition to the cathode layers. The anode layers and cathode layers may be separated into tab groups and positioned in the space between the top of the stack and the housing and the face of the stack and the housing. The anode layers and cathode layers remain separated from each other such as with paper layers. Insulation may also be required between the anode and cathode layers and the case.

Figure 29:
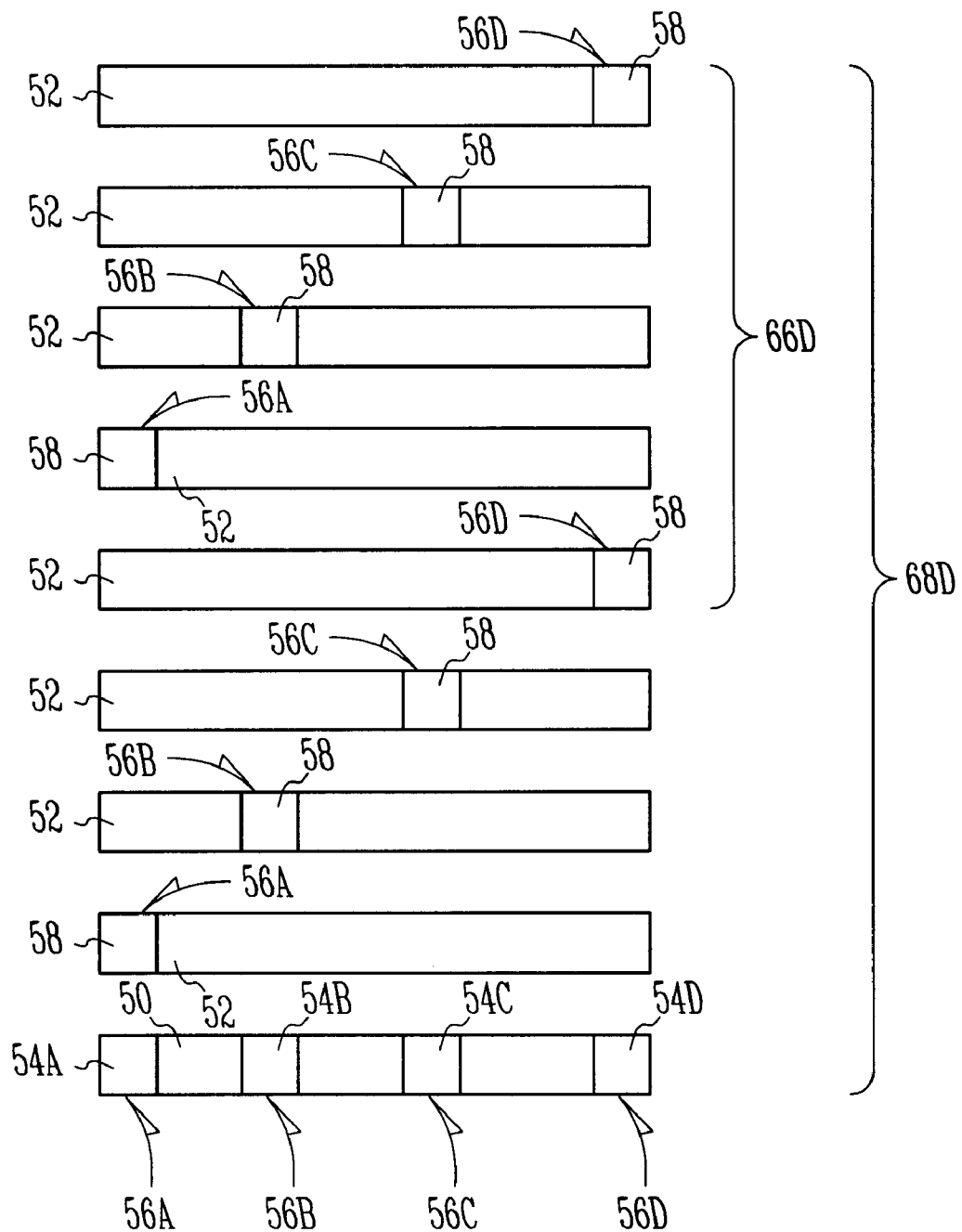
FIG. 29 is a partial exploded side view of the capacitor stack of FIG. 26.

FIG. 29 shows a side view of base layer 50 and secondary layers 52 of a capacitor stack including layer groups such as non-adjacent layer group 66d. The matching tabs 58 of secondary layers 52 of non-adjacent layer group 66d are shown mating with base tab 54d to form non-adjacent tab group 68d.

Figure 30:
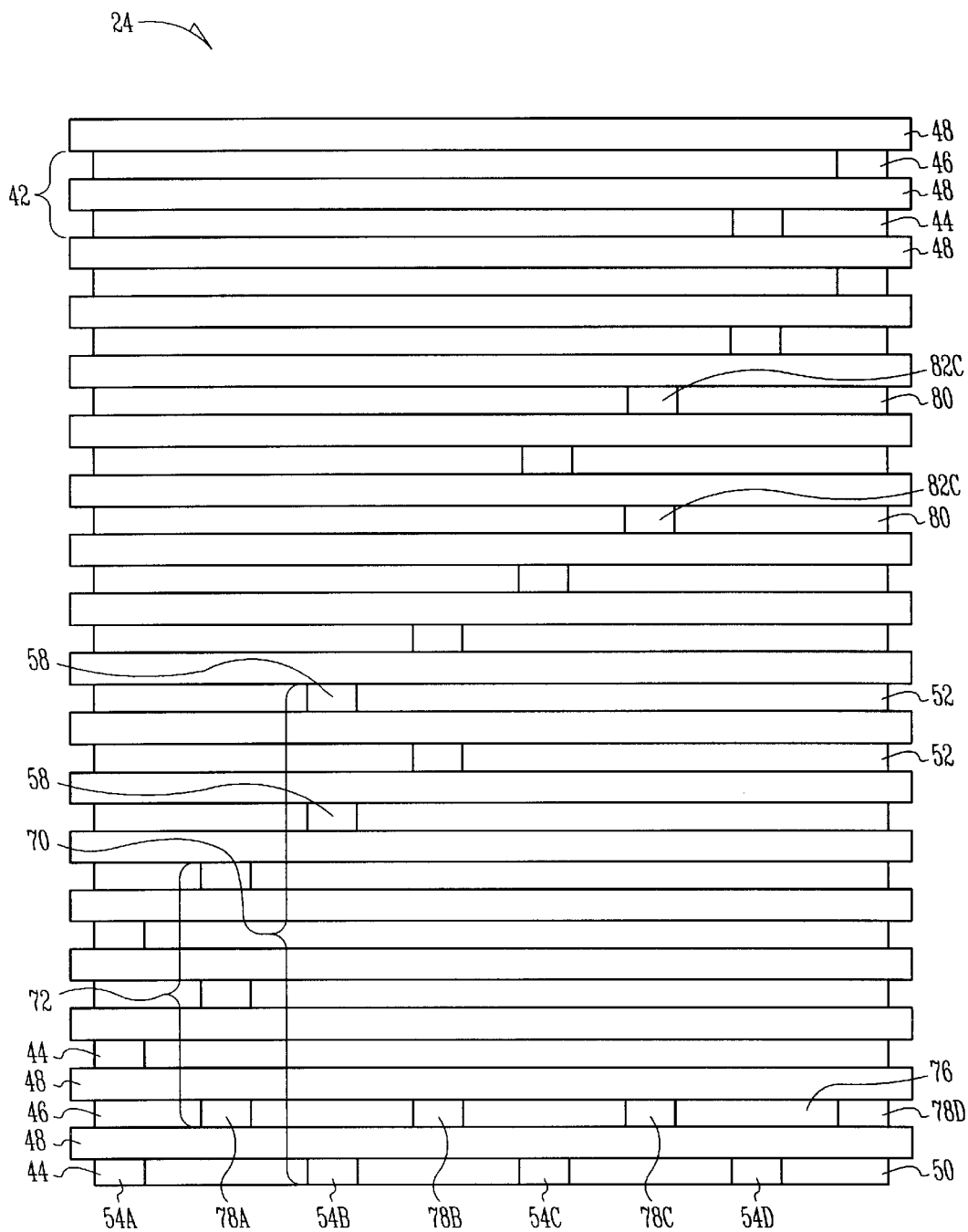
FIG. 30 is a partial side view of a capacitor stack according to one embodiment.

FIG. 30 shows a side view of the foil layers of a capacitor stack 24 according to one embodiment where both one or more anode layers 46 and one or more cathode layers 44 are portioned into cathode tab groups 70 and anode tab groups 72.

Capacitor stack 24 comprises separators 48 between foil layers of alternating cathode layers 44 and anode layers 46. The anode layers and cathode layers form capacitive elements 42. The cathode layers include a base layer 50 and secondary layers 52. The base layer 50 has base tabs 54a–54d and the secondary layers 52 have matching tabs 58. Each matching tab 58 overlays one of the base tabs 54a–54d of the base layer 50. The cathode layers 44 connect to the base layer 50.

The anode layers 46 include a secondary base layer 76 with secondary base tabs 78a–78d and additional secondary layers 80. Each of the additional secondary layers 80 has a secondary matching tab 82 with each secondary matching tab 82 overlaying one of the secondary base tabs 78a–78d of the secondary base layer 76. For example, secondary matching tab 82c vertically matches or overlays secondary base tab 78c. Each of the anode layers 46 connect to the secondary base layer 76.

In one or more of the embodiments described above, the foil layers are spread out or distributed over multiple locations. For example, the cathode layers may be spread out over four locations with four tab groups, with the thickness of each tab group at each location being about 0.006 inch (assuming that 5 layers at 0.00118 inch per layer are at each location). This thinness of the tab group allows the stacked unit to be placed into the housing with the tab groups occupying the space between the housing and the edge of the stack or the clearance space between the lid and the top of the stack. These clearance spaces are allowed for inserting the stack into the housing. As a comparison, if the cathode tabs were all brought out at one location, the thickness would be greater than 0.020 inch and make it difficult, if not practically impossible, to fold the tabs collectively over the stack as in FIGS. 27 and 28. Thus, this thickness would require that part of the stack be removed or the case enlarged to allow space for routing and connecting the cathode layer connections, thereby reducing the packing efficiency of the capacitor.

One embodiment of a method to cut foil layers out of etched and unetched aluminum foil using a laser is described below. In one embodiment, the method of preparing aluminum foil layers for electrolytic capacitors includes cutting a capacitor foil layer out of a sheet of aluminum foil with a laser, removing the foil layer from the sheet of aluminum foil, and inserting the foil layer shape in a capacitor. The foil layer may be used as a cathode layer or as an anode layer. In some embodiments, the foil layer includes a plurality of tabs.

In various embodiments, the cutting may be partially through the sheet, the method may include cutting multiple sheets at one time, the method may include cutting multiple layers of sheets including paper separators, and/or the method may include cutting a portion or an entire capacitor stack at one time.

In some embodiments, the method includes laying out a pattern of capacitor foil layer shapes, delivering the aluminum foil to the laser in a roll, cutting different shapes out of the sheet of aluminum foil, and cutting through multiple layered sheets of aluminum foil. The method is used to cut out the intricate shapes of a multi-leg or multi-tab foil layer.

Using the above laser cutting method has one or more of the following advantages: a) rapid prototyping, b) the cut out shape does not drop out of the foil until needed, making for easier handling, c) the method eliminates the need for constant sharpening of expensive dies, d) the method does not produce burrs or particulates. Thus, allowing the use of thinner separators, e) the method allows for optimal pattern layout on the foil reducing the amount of generated waste, f) the foil may be delivered to the laser in several ways including rolls, sheets or small pieces, and g) the laser can be set up to cut out different shapes out of the shame sheet. The method has the advantage of cutting out the intricate shapes of the multiple tab cathode described above without tearing the closely spaced tabs. In addition, the intricate shapes can be formed without developing an expensive die that requires sharpening.

In one embodiment, the foil is cut using a Signature 75 laser manufactured by Control Laser Corporation. In various embodiments, the laser was set at the following setting: current 18–23, 5–8 kHz, and a speed of 0.35 to 1.5 inches/second.

Figure 31:
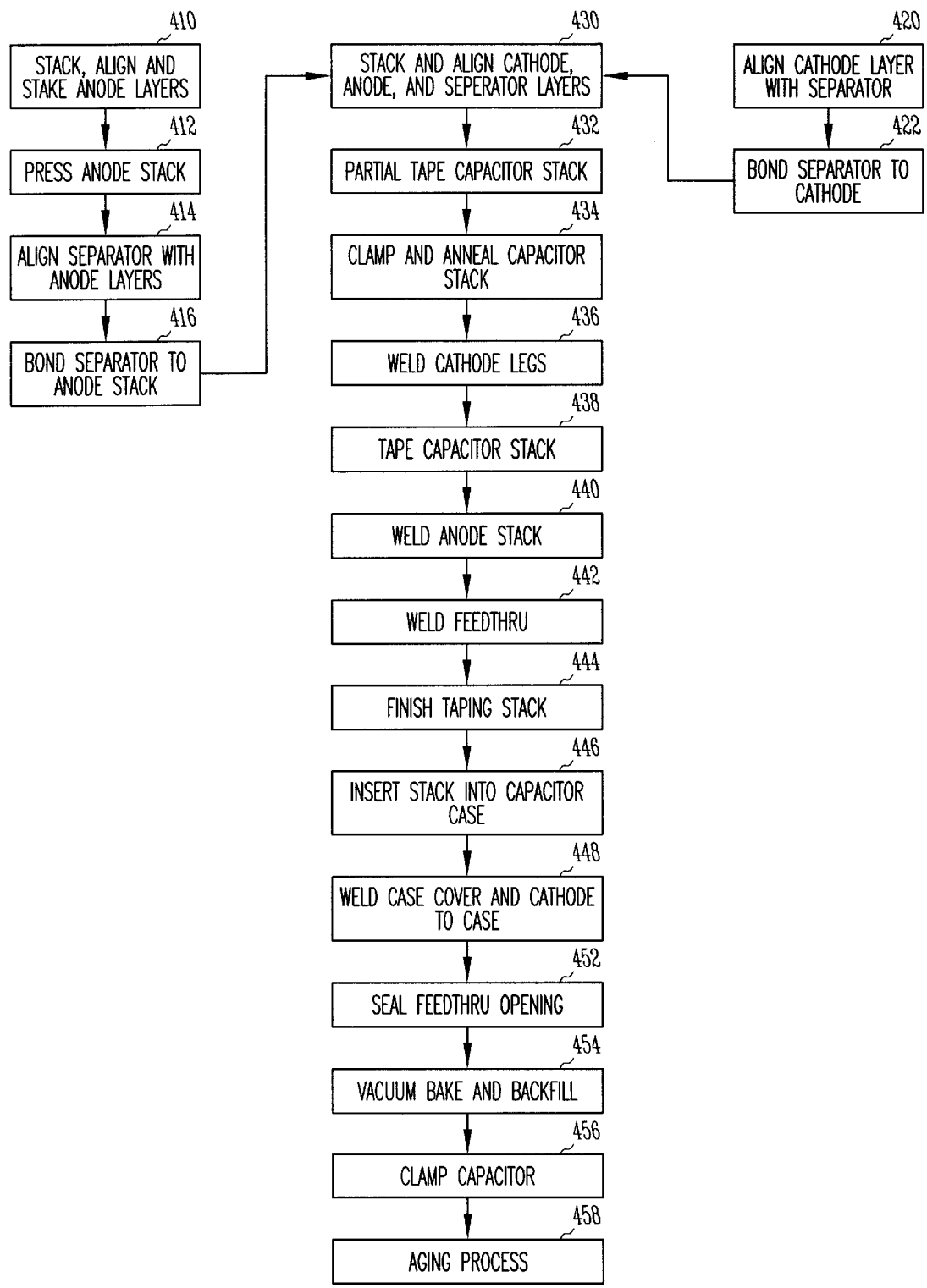
FIG. 31 is a flow chart of a method for manufacturing a capacitor in accordance with one embodiment.

FIG. 31 illustrates an example of a process flow for a method for manufacturing a capacitor 18 having a capacitor stack 24 with one or more of the features described above. The method of FIG. 31 is an example of one embodiment and it is understood that different steps may be omitted, combined, and/or the order changed within the scope of one or more embodiments of the present invention.

The method includes, at 410, stacking the anode conductive layers within an external alignment mechanism 408 and aligning them therein. In some embodiments, the anode stack is pressed 412, as further described below. The separator is aligned with the anode layers 414, and the separator is coupled with the anode stack 416, for example, by bonding using, for example, an adhesive. The cathode layer is aligned with the cathode separator at 420, and the cathode separator is coupled with the cathode layer at 422, for example, by bonding the cathode separator with the cathode layer using, for example, an adhesive.

In one embodiment, the anode stack and cathode stack are individually pressed to improve the flatness of each stack and to reduce or eliminate warpage, and are optionally are pressed to a specific, predetermined height. In another option, the capacitor stack 24 is pressed to improve the flatness and to reduce or eliminate warpage. In one embodiment, the capacitor stack 24 is pressed to a specific height to improve the flatness and to reduce or eliminate warpage. Pressing to a specific height helps to maintain consistency in the manufacturing process. Each anode stack 100, each cathode stack 300–304, each layer set, the capacitor stack 24 of all of the layer sets form, in effect, a spring. The spring rate will vary from capacitor stack 24 to capacitor stack 24 due, in part, to variations in the foil supplied and/or in the manufacturing processes associated with cutting the foil as well as the general handling of the part. Pressing the anode stack 100, the cathode stacks 300–304, the layer set, or the capacitor stack 24 to a controlled height maintains consistency in the assembly process in that each stack 100, 300–304, layer set or capacitor stack 24 will be maintained at the same height regardless of initial spring rate. Among other things, this assures a consistent fit between the capacitor stack 24 and the case 20 (FIG. 1).

Referring again to FIG. 18, at 430, the cathode, anode, and separator layers are stacked and aligned by the outer edges of the separators using the external alignment mechanism 400 to form a capacitor stack 24. The capacitor stack 24 is optionally partially taped at 432. Optionally, at 434 the capacitor stack is clamped and annealed. For example, an anode stack is pressed to a specified height, then assembled into the capacitor stack 24. The capacitor stack 24 is clamped to a specified height and annealed. In one example, annealing includes heating to a temperature of about 85° C., soaking for about 12 hours, and cooling to 23° C. degrees for about 1 hour.

In another option, the components are individually annealed. Annealing reduces or eliminates undesired residual stresses which contribute to warpage and can help to provide improved flatness of the overall capacitor stack 24. Annealing can also be performed after a portion of an electrode has been deformed to retain the deformed shape and reduce effect of material relaxation. In applications where the anode conductive layers are deformed annealing after deforming can also reduce creation of discontinuities of the dielectric layer on the deformed portion of an anode stack. Annealing reduces stresses, increases softness and ductility and produces a specific microstructure. A variety of annealing heat treatments can be applied to the components of the capacitor to accomplish the desired result.

Further processing includes welding the cathode legs 436, taping the capacitor stack 438, welding the anode stack 440, and welding the feedthrough 442, and finish taping the capacitor stack 444. In addition, the capacitor stack is inserted into the capacitor case 446, the case cover and the cathode ribbon are welded to the case at 448. The feedthrough opening is sealed at 452. The process further includes a vacuum bake and backfill at 454, clamping the capacitor at 456, and an aging process at 458.

Figure 32:
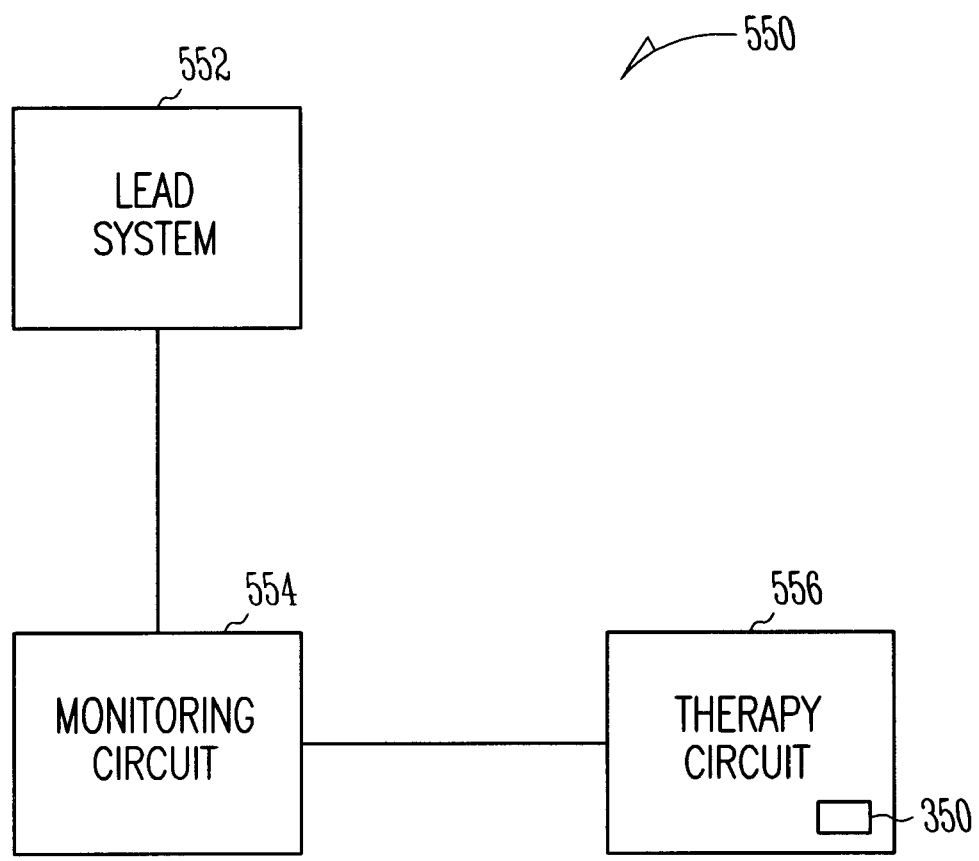
FIG. 32 is a block diagram of a implantable medical device system constructed in accordance with one embodiment.

FIG. 32 illustrates one of the many applications for the capacitor. For example, one application includes an implantable medical device 550 which provides therapeutic stimulus to a heart muscle, for instance, a defibrillator. The medical device 550 is coupled with a lead system 552. The lead system 552 is implanted in a patient and electrically contacts strategic portions of a patient's heart. The medical device 550 further includes a monitoring circuit 554 for monitoring heart activity through one or more of the leads of the lead system 552. The medical device 550 further includes a therapy circuit 556 which includes one or more capacitors 350 having one or more of the features of the capacitors discussed above. The therapy circuit 556 delivers a pulse of energy through one or more of the leads of lead system 552 to the heart, where the medical device 550 operates according to well known and understood principles.

In addition to implantable defibrillators, the capacitor can be incorporated into other cardiac rhythm management systems, such as heart pacers, combination pacer-defibrillators, congestive heart failure devices, and drug-delivery devices for diagnosing or treating cardiac arrhythmias. Moreover, the capacitor can be incorporated also into non-medical applications, for example, photographic flash equipment. Alternatively, one or more teachings of the present discussion can be incorporated into cylindrical capacitors.

It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present invention. The scope of the invention should, therefore, be determined with reference to the appended claims, along with the full scope of equivalents to which such claims are entitled.

What is claimed is:

1. A method of manufacturing a flat capacitor stack, comprising:
    forming a plurality of capacitor layers, each capacitor layer including a separator layer attached to a capacitor foil layer; and
    placing each of the plurality of capacitor layers onto a capacitor stack by aligning each of the capacitor layers using an outer edge of the separator layer of the capacitor layer as an alignment means.

2. The method of claim 1, wherein aligning includes positioning the separator layer such that two or more points on an outer edge of the separator layer contact two or more corresponding alignment members.

3. The method of claim 1, further comprising pressing the capacitor stack to a specified, predetermined height after the capacitor stack has been formed.

4. The method of claim 1, further comprising annealing the capacitor stack after the capacitor stack has been formed.

5. The method of claim 1, wherein placing each of the plurality of capacitor layers includes:

providing an alignment mechanism; and placing each capacitor layer within the alignment mechanism such that an outer edge of each separator layer contacts one or more alignment members of the alignment mechanism.

6. The method of claim 1, wherein forming a plurality of capacitor layers includes forming a first anode stack having or more anode layers and having a first surface area, and forming a second anode stack having or more anode layers and having a second surface area, wherein the first surface area is greater than the second surface area.

7. The method of claim 6, wherein the second anode stack has one or more less anode layers than the first anode stack.

8. A flat capacitor having a capacitor stack formed by a method including:

forming a plurality of capacitor layers, each capacitor layer including a separator layer attached to a capacitor foil layer; and placing each of the plurality of capacitor layers onto a capacitor stack by aligning each of the capacitor layers using an outer edge of the separator layer of the capacitor layer as an alignment means.

9. The flat capacitor of claim 8, wherein aligning the separator layer includes positioning the separator layer such that two or more points on an outer edge of the separator layer contact two or more corresponding two or more alignment members.

10. The flat capacitor of claim 8, further comprising pressing the capacitor stack to a specified, predetermined height.

11. The flat capacitor of claim 8, further comprising annealing the capacitor stack.

12. The flat capacitor of claim 8, wherein aligning each of the plurality of capacitor layers includes:

providing an alignment mechanism; and placing each capacitor layer within the alignment mechanism such that an outer edge of each separator layer contacts one or more alignment members of the alignment mechanism.

13. The flat capacitor of claim 8, wherein at least one of the plurality of capacitor layers includes a first anode stack having or more anode layers and having a first surface area, and wherein at least one of the plurality of capacitor layers includes a second anode stack having or more anode layers and having a second surface area, wherein the first surface area is greater than the second surface area.

14. The flat capacitor of claim 13, wherein the second anode stack has one or more less anode layers than the first anode stack.

* * * * *